(12) United States Patent
Zhang et al.

(10) Patent No.: US 12,018,262 B2
(45) Date of Patent: Jun. 25, 2024

(54) METHOD FOR PRODUCING WASHING ENZYME HAVING PROTEASE RESISTANCE

(71) Applicant: QINGDAO VLAND BIOTECH GROUP CO., LTD, Shandong (CN)

(72) Inventors: Qing Zhang, Shandong (CN); Zhibing Chen, Shandong (CN); Yanping Liu, Shandong (CN); Yanjun Tian, Shandong (CN); Wei Xu, Shandong (CN); Yinan Guan, Shandong (CN); Yijun Huang, Shandong (CN); Jiahua Lyu, Shandong (CN)

(73) Assignee: QINGDAO VLAND BIOTECH GROUP CO., LTD, Shandong (CN)

( * ) Notice: Subject to any disclaimer, the term of this patent is extended or adjusted under 35 U.S.C. 154(b) by 370 days.

(21) Appl. No.: 17/288,530

(22) PCT Filed: Oct. 28, 2019

(86) PCT No.: PCT/CN2019/113627
§ 371 (c)(1),
(2) Date: Apr. 24, 2021

(87) PCT Pub. No.: WO2020/088393
PCT Pub. Date: May 7, 2020

(65) Prior Publication Data
US 2022/0010315 A1    Jan. 13, 2022

(30) Foreign Application Priority Data

Oct. 31, 2018 (CN) .......................... 201811285860.9

(51) Int. Cl.
| | | |
|---|---|---|
| *C12N 15/62* | (2006.01) | |
| *C07K 14/81* | (2006.01) | |
| *C12N 9/20* | (2006.01) | |
| *C12N 9/42* | (2006.01) | |
| *C12N 9/96* | (2006.01) | |

(52) U.S. Cl.
CPC ............ *C12N 15/62* (2013.01); *C07K 14/811* (2013.01); *C12N 9/20* (2013.01); *C12N 9/2437* (2013.01); *C12N 9/96* (2013.01)

(58) Field of Classification Search
CPC ......... C12N 15/62; C12N 9/2437; C12N 9/20
See application file for complete search history.

(56) References Cited

U.S. PATENT DOCUMENTS

| | | | |
|---|---|---|---|
| 5,527,487 A | 6/1996 | Mikkelsen et al. | |
| 7,413,877 B2 * | 8/2008 | Collier .................... | A61P 19/02 |
| | | | 435/71.1 |
| 8,241,885 B2 * | 8/2012 | Bryan ...................... | C12N 9/54 |
| | | | 435/68.1 |
| 2001/0036911 A1 | 11/2001 | Davis et al. | |
| 2009/0181874 A1 | 7/2009 | Souter et al. | |
| 2018/0171271 A1 | 6/2018 | Skagerlind et al. | |
| 2019/0382690 A1 | 12/2019 | Mole et al. | |

FOREIGN PATENT DOCUMENTS

| | | |
|---|---|---|
| CA | 2392158 A1 | 6/2001 |
| CN | 1238805 A | 12/1999 |
| CN | 101909595 A | 12/2010 |
| CN | 104789543 A | 7/2015 |
| CN | 107922896 A | 4/2018 |
| CN | 108291179 A | 7/2018 |
| WO | 9813483 A1 | 4/1998 |
| WO | 0001831 A2 | 1/2000 |

OTHER PUBLICATIONS

International Search Report for PCT/CN2019/113627 dated Jan. 19, 2020, ISA/CN.
The 1st Office Action dated Jul. 27, 2022 for the Chinese Patent Application No. CN201980029782.2.
Keranen et al., 1995—"Production of recombinant proteins in the filamentous fungus Trichoderma reesei", Current Opinion in Biotechnology, vol. 6, No. 6, Jan. 1, 1995.
The European search report dated Aug. 23, 2022 for EP19877863.1.

* cited by examiner

*Primary Examiner* — Suzanne M Noakes
(74) *Attorney, Agent, or Firm* — Yue (Robert) Xu; Apex Attorneys at Law, LLP

(57) ABSTRACT

Provided is a method for producing washing enzyme having protease resistance. According to the method, the washing enzyme having resistance to protease is obtained by carrying out fusion expression on a gene of the washing enzyme with the gene of a protease inhibitory peptide, thereby facilitating maintaining the stability of various enzyme components in an enzyme-containing detergent, and improving the use effect of the detergent.

7 Claims, 1 Drawing Sheet
Specification includes a Sequence Listing.

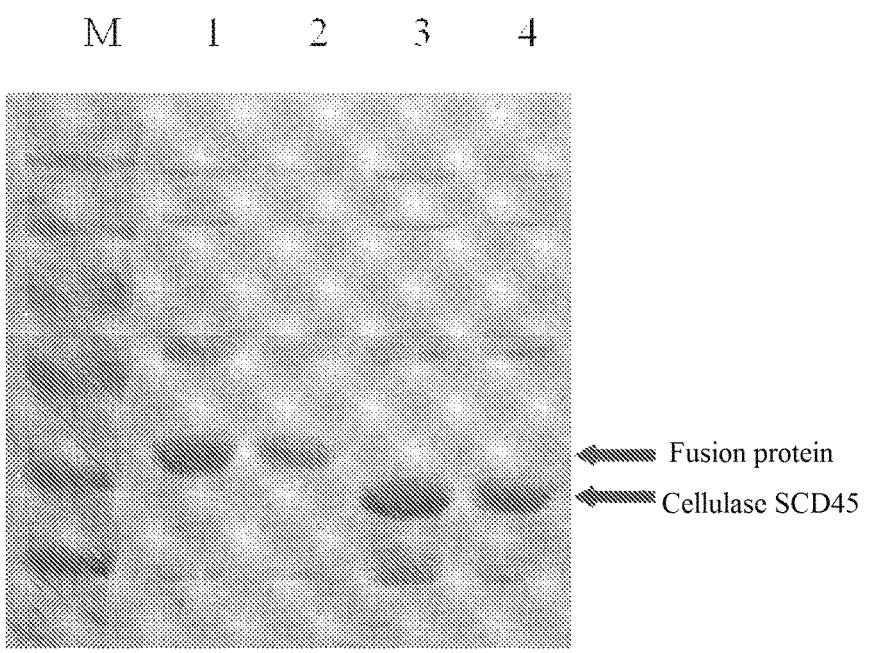

METHOD FOR PRODUCING WASHING ENZYME HAVING PROTEASE RESISTANCE

CROSS REFERENCE TO RELATED APPLICATIONS

This application is a US National Phase application based upon PCT Application No. PCT/CN2019/113627 filed Oct. 28, 2019, which claims the priority of Chinese Patent Application No. 2018112858609, filed to China National Intellectual Property Administration on Oct. 31, 2018, and titled with "METHOD FOR PRODUCING WASHING ENZYME HAVING PROTEASE RESISTANCE", and the disclosures of which are hereby incorporated by reference.

FIELD

The present disclosure relates to the technical field of genetic engineering, and specifically to a method for producing a laundry enzyme with protease resistance by fusion expression of a gene encoding a laundry enzyme and a gene encoding a protease inhibitory peptide.

BACKGROUND

As early as 1913, Rohm had used pancreatic extract in the detergent component for pre-soaking, Burnus, and created the history of the application of biological enzymes in the detergent industry. The commercialized laundry enzymes abroad are mainly hydrolytic enzymes including alkaline protease, amylase, alkaline cellulase, lipase, and combinations thereof. Newly developed oxidoreductases (such as catalase) with anti-dye transfer function or disinfection and sterilization effect also have good application prospects.

Using the biological enzyme as a detergent auxiliary is one of the major technological advances in the development of synthetic detergent industry, including promoting the sustainable development of detergent industry, reducing the dosage of a surfactant and sodium tripolyphosphate in detergent to thereby contribute to the development of low-phosphorus or non-phosphorus detergent, improving the detergent performance, decreases the emission of pollutants due to the non-toxic and completely biodegradable properties of the biological enzyme, and reducing the washing temperature and the number of rinsing so as to save energy and water.

However, due to the easy degradation of biological enzymes, the complexity of detergent formulation technology, and the influence of formulation components such as surfactants, bleaching agents and proteases and formulation conditions such as pH and temperature, the stability of enzymes has become an outstanding problem of enzyme-containing detergent formulation. Enzyme manufacturers and detergent developers use comprehensively technologies such as protein engineering technology, chemical modification technology, stabilizer addition and microencapsulation technology to improve the stability of enzymes in detergent so as to improve their effects.

In liquid detergent containing large amounts of water, enzymes are usually unstable. The solvent, buffer, charged surfactant and other components of the formulation may lead to unfolding of the tertiary structure of the enzyme during storage. What is more, the protease is more likely to degrade other enzymes in aqueous solution. During storage of liquid laundry products, more and more enzymes are inactivated over time due to the hydrolysis of protease on itself and on other enzymes. Therefore, addition of an appropriate amount of stabilizing medium to inhibit protease activity, adjust charge balance, strengthen osmotic protection, and therefore ensure the structure rigidity of biological enzyme is the main technical solution to solve the problem of enzyme stability in liquid detergents, and is called stabilizer addition technology. The current focus of this technology is the development of an efficient protease inhibitor and a compound stable system suitable for formulations.

It has long been known that phenylboronic acid and isomers thereof can reversibly inhibit the activity of a variety of proteases. During the storage of liquid detergents, the addition of borate compounds can effectively inhibit the activity of protease to prevent it from hydrolyzing itself and other enzymes so as to avoid the loss of enzymatic activity during product storage. During the washing process, with the dilution of detergent, the enzymatic activity can be quickly and effectively restored. Since the 21st century, Novozymes and Procter & Gamble have both focused on the development of aryl-containing organic borates as protease inhibitors. However, animal experiment results indicated borate as the second type of reproductive toxicity compound. Then the researchers found that in the protease-containing liquid detergent, α-hydroxy carboxylate plays a key role in the stability of the enzyme, especially the aryl-containing carboxylate derivatives, which are more effective and become a new generation of protease inhibitor mainstream products. Novozymes has developed 3-chlorobenzoic acid, 4-chlorobenzoic acid, 3-chlorophenylacetic acid, 3,5-dichlorobenzoic acid and other aryl-containing carboxylate derivatives as subtilisin inhibitor, which has better biodegradability than borate. Although the amount of such protease inhibitors added in detergents is much lower than that of borate protease inhibitors, as compounds containing aryl group, their long-term use will cause certain adverse effects on the natural environment and animal health. Therefore, those skilled in the art are actively looking for a protease inhibitor that is environmentally friendly and has no toxic and side effects or developing new methods to improve the stability of enzyme.

SUMMARY

In order to solve such technical issues, the present disclosure provides a method for producing a laundry enzyme with protease resistance. According to the method, the laundry enzyme with protease resistance is obtained by fusion expression of a gene encoding a laundry enzyme and a gene encoding a protease inhibitory peptide, to provide the laundry enzyme with protease resistance which is beneficial to maintain the stability of various enzyme components in an enzyme-containing detergent and improve the use effect of the detergent.

The present disclosure provides a method for producing a laundry enzyme with protease resistance, comprising:
(a) constructing a fusion polynucleotide sequence comprising a gene encoding a laundry enzyme and a gene encoding a protease inhibitory peptide;
(b) introducing the sequence into a host cell;
(c) culturing the host cell, expressing the sequence and producing a fusion protein of laundry enzyme-protease inhibitory peptide, wherein the fusion protein is the laundry enzyme with protease resistance.

The laundry enzyme and the protease inhibitory peptide in the fusion protein are fused covalently.

The laundry enzyme is any one selected from the group consisting of cellulase, lipase, cutinase, amylase, glucoamylase, pectinase, mannanase, arabinase, galactosidase, xylanase, laccase and peroxidase.

Preferably, the laundry enzyme is cellulase.

Preferably, the laundry enzyme is lipase.

The protease inhibitory peptide is any one or two or three selected from the group consisting of *Streptomyces* subtilisin inhibitor (SSI) derived from *Streptomyces* sp., Bowman-Birk protease inhibitor (BBI), protease inhibitory peptide PCL derived from Barley, protease inhibitor marinostatin (MST) derived from *Alteromonas* and a propeptide derived from *Bacillus* sp.

The host cell is *Bacillus* sp., *Aspergillus* sp., *Trichoderma* sp., *Pichia pastoris, Saccharomyces cerevisiae* or *Escherichia coli*.

Preferably, the host cell is *Trichoderma* sp., and more preferably, the host cell is *Trichoderma reesei*.

The protease inhibitory peptide can be fused to the laundry enzyme in the N-terminus, C-terminus or middle of the fusion protein.

The present disclosure also provides a laundry enzyme with protease resistance produced by the method described herein.

The present disclosure also provides use of the laundry enzyme with protease resistance described herein in a detergent.

The fusion expression of cellulase or lipase and protease inhibitor peptide of the present disclosure significantly improves the protease resistance and effectively reduces the degradation effect of protease on cellulase or lipase. In the presence of protease, after storage at room temperature for 12 h the residual enzymatic activity of cellulase SCD45 is 91.4%, while that of the fusion protein of cellulase SCD45-protease inhibitory peptide is 99.7%; after storage at 40° C. for 24 h, the residual enzymatic activity of cellulase SCD45 is only 8.1%, while that of the fusion protein of cellulase SCD45-protease inhibitory peptide is 74.0%, which is significantly improved.

The cellulase with protease resistance provided by the present disclosure can be wildly used in detergents to increase the stability of enzymes. After storage at 37° C. for 24 h, the residual enzymatic activity of cellulase in an enzyme-containing detergent added with cellulase SCD45 is 12.1%, while that of cellulase in an enzyme-containing detergent added with the fusion protein of cellulase SCD45-protease inhibitory peptide is 59.5%. After storage at 37° C. for 48 h, the residual enzymatic activity of cellulase in an enzyme-containing detergent added with cellulase SCD45 is 2.1%, while that of cellulase in an enzyme-containing detergent added with the fusion protein of cellulase SCD45-protease inhibitory peptide is 28.9%. After storage at 37° C. for 72 h, the residual enzymatic activity of cellulase in an enzyme-containing detergent added with cellulase SCD45 is 0.9%, while that of cellulase in an enzyme-containing detergent added with the fusion protein of cellulase SCD45-protease inhibitory peptide is 14.2%, which is significantly improved and achieves unexpected technical effects. The protease resistance of cellulase HGD45 and cellulase NT45 are also significantly improved by fusion expression with a gene of a protease inhibitory peptide.

The residual enzymatic activities of the fusion protein of lipase TG-protease inhibitory peptide after storage at 37° C. for 2d, 5d and 6d are all significantly improved compared with those of lipase TG. Especially, after storage for 6d, the residual enzymatic activity of the fusion protein is 64.6%, which is 86.7% higher than that of lipase TG, achieving a very significant effect.

In addition to cellulase and lipase, the method described in the present disclosure can be widely used in other laundry enzymes, such as cutinase, amylase, pectinase, mannanase, arabinase, galactosidase, xylanase, laccase and peroxidase, etc., to significantly improve the protease resistance of these enzymes to reduce the degradation effect of the protease on them, and achieve coexistence of above-mentioned enzymes and protease in the detergent.

BRIEF DESCRIPTION OF DRAWINGS

FIG. 1 shows the SDS-PAGE electrophoretogram, where Lane M represents Marker, Lane 1 and Lane 2 are the fermentation supernatants of *Trichoderma reesei* PS, and Lane 3 and Lane 4 are the fermentation supernatants of *Trichoderma reesei* SCD45.

DETAILED DESCRIPTION

The present disclosure will now be described in detail by reference to the following definitions and examples. Unless defined otherwise herein, all technical and scientific terms used herein have the same meaning as commonly understood by one of ordinary skill in the art to which the present disclosure belongs. P Singleton et al., DICTIONARY OF MICROBIOLOGY AND MOLECULAR BIOLOGY, Second Edition, John Wiley and Sons, New York, 1994, and Hale & Marham, THE HARPER COLLINS DICTIONARY OF BIOLOGY, published by Harper Perennial, New York, 1991 provide one of skill with a general dictionary of many terms used in the present disclosure. Although any methods and materials similar or equivalent to those described herein can be used in the practice or testing of the present disclosure, the preferable methods and materials are described in the present disclosure. Numeric ranges are inclusive of the numbers defining the range. Unless otherwise indicated, the nucleic acid sequence is written from left to right in the 5' to 3' direction and the amino acid sequence is written from left to right in the amino end to carboxyl end direction, respectively. In particular, practitioners can refer to Sambrook et al., 1998, and Ausubel F M et al., 1993, for definitions and terms in the art. It should be understood that the present disclosure is not limited to the particular methodology, protocols, and reagents described herein, as these may vary.

As used herein, a "fusion protein of laundry enzyme-protease inhibitory peptide" refers to a protein formed by the fusion of at least one molecule of a laundry enzyme (or fragment or variant thereof) with at least one molecule of a protease inhibitory peptide (or fragment or variant thereof). The fusion protein of laundry enzyme-protease inhibitory peptide comprises at least a fragment or variant of a laundry enzyme and at least a fragment or variant of a protease inhibitory peptide, which are linked to each other by, e.g., genetic fusion (i.e., the fusion protein of laundry enzyme-protease inhibitory peptide is generated by translation of a nucleic acid in which a polynucleotide encoding all or a portion of a protease inhibitory peptide is linked to a polynucleotide encoding all or a portion of a laundry enzyme in the same reading frame). The laundry enzyme and protease inhibitory peptide, once being a part of the fusion protein, may be referred to as a "portion", "region", or "moiety" of the fusion protein.

The present disclosure will be described in detail in conjunction with the following examples.

Example 1 Improve Protease Resistance by Expressing Fusion Protein of Cellulase SCD45 and *Streptomyces* Subtilisin Inhibitor (SSI)

1.1 Generation of the Fusion Gene of Cellulase SCD45-*Streptomyces* Subtilisin Inhibitor (SSI)

The gene of cellulase SCD45 is fused with the gene of inhibitor SSI derived from *Streptomyces* sp., to generate the fusion gene of cellulase SCD45-*Streptomyces* subtilisin inhibitor (SSI).

The amino acid sequence of cellulase SCD45 is shown as SEQ ID NO: 1, and the encoding polynucleotide sequence thereof is shown as SEQ ID NO: 2.

The amino acid sequence of *Streptomyces* subtilisin inhibitor (SSI) is shown as SEQ ID NO: 3, and the encoding polynucleotide sequence thereof is shown as SEQ ID NO: 4.

The gene of cellulase SCD45 and the gene of *Streptomyces* subtilisin inhibitor (SSI) were separately synthesized by Suzhou Genewiz Biotechnology Co., Ltd.

The specific procedures were as follows:

The gene fragment encoding cellulase SCD45 was amplified by PCR amplification reaction with cellulase SCD45 gene as a template using primer 1 (shown as SEQ ID NO: 7) and primer 2 (shown as SEQ ID NO: 8).

The gene fragment encoding subtilisin inhibitory peptide SSI was amplified by PCR reaction with *Streptomyces* subtilisin inhibitor (SSI) gene as a template using primer 3 (shown as SEQ ID NO: 9) and primer 4 (shown as SEQ ID NO: 10).

The purified U-Clone fragments of cellulase SCD45 and the purified U-Clone fragments of *Streptomyces* subtilisin inhibitor (SSI) were mixed in equal molar ratio. The fusion gene of cellulase SCD45-*Streptomyces* subtilisin inhibitor (SSI) was generated by PCR amplification reaction with the above U-Clone fragment mixture as a template using primer 1 and primer 4, and was named SCD45-SSI. The fusion gene comprises a polynucleotide sequence shown as SEQ ID NO: 6 and codes an amino acid sequence shown as SEQ ID NO: 5, in which *Streptomyces* subtilisin inhibitor (SSI) was fused to the C-terminus of cellulase SCD45. The PCR reaction was carried out for 30 cycles of 94° C. for 40 seconds, 62° C. for 40 seconds, and 72° C. for 1 minute. After the final extension at 72° C. for 5 min, the products were stored at 16° C.

1.2 Construction of Expression Vector

The SCD45-SSI fusion gene fragment synthesized above was cloned into the *Trichoderma* expression plasmid pSC2G after double digestion with Xba I and Mlu I by using the U-Clone kit to construct the recombinant expression plasmid named SCD45-SSI-pSC2G. To ensure accuracy, several clones were sequenced for verification. The recombinant expression plasmid with cellulase SCD45 gene was constructed by the same method as mentioned above and named SCD45-pSC2G.

1.3 Construction and Screening of the *Trichoderma reesei* Engineering Strain (1) Preparation of Protoplasts The spore suspension of the host cell *Trichoderma reesei* SCHD4 were plated onto a PDA plate and cultured at 30° C. for 6 days. After the spores were abundant, about 1 cm×1 cm of the colony was cut and placed in a liquid medium containing 120 mL YEG+U (0.5% yeast powder, 1% glucose, 0.1% uridine) and then cultured at 30° C. for 14-16 h with shaking at 220 rpm.

The mycelia were filtered with aseptic gauze and washed once with aseptic water. The mycelia were placed in a flask containing 20 mL of 10 mg/mL lyase solution (Sigma L1412) at 30° C. for 1-2 h with shaking at 90 rpm. The progress of protoplast transformation was observed using microscope.

20 mL of pre-cooled 1.2M sorbitol (1.2M sorbitol, 50 mM Tris-Cl, 50 mM $CaCl_2$) was added to the above flask and shaken well gently. The filtrate was collected by using the aseptic Miracloth filter cloth and then was centrifuged at 3000 rpm at 4° C. for 10 min. The supernatants were removed, and the pellets were re-suspended in 5 mL of pre-cooled sorbitol solution (1.2M) and then centrifuged at 3000 rpm at 4° C. for 10 min. The supernatants were removed, and the pellets were re-suspended in a suitable amount of pre-cooled sorbitol (1.2M) and subpackaged (200 μL in each tube, with a protoplast concentration of $10^8$/mL).

(2) Transformation of Expression Vector and Strain Verification

The following operations were performed on ice. 10 μg of recombinant plasmid SCD45-SSI-pSC2G was added to a 7 mL aseptic centrifuge tube containing 200 μL of protoplast solutions. Then, 50 μL of 25% PEG (25% PEG, 50 mM Tris-Cl, 50 mM $CaCl_2$) was added and mixed well by flicking the bottom of tube gently and placed for 20 min on ice. Next, 2 mL of 25% PEG was added and mixed well and placed at room temperature for 5 min. After that, 4 mL of 1.2M sorbitol were added and mixed well gently. Then the mixture was poured into the melted upper medium (0.1% $MgSO_4$, 1% $KH_2PO_4$, 0.6% $(NH_4)_2SO_4$, 1% glucose, 18.3% sorbitol, 0.35% agarose) maintained at 55° C. After mixing gently, the mixture was spread on the prepared lower culture medium plate (2% glucose, 0.5% $(NH_4)_2SO_4$, 1.5% $KH_2PO_4$, 0.06% $MgSO_4$, 0.06% $CaCl_2$, 1.5% Agar) and cultured at 30° C. for 5 days until the transformants appeared.

The transformants were picked to the lower culture medium plate and cultured at 30° C. for 2 days. An appropriate amount of mycelium was put in a 2 mL centrifuge tube, and 100 mg of aseptic quartz sand and 400 μL of extraction buffer (100 mM Tris-HCl, 100 mM EDTA, 250 mM NaCl, 1% SDS) were added, and shaken violently by minibeadbeater for 2 min. After keeping in a water bath at 65° C. for 10 min, 200 μL of 10 M $NH_4AC$ was added. The tube was then put on ice for 10 min and centrifuged at 13000 rpm for 10 min. The supernatants were transferred into a new tube and added with 2 volumes of absolute ethanol, and then placed at −20° C. for 30 min. After centrifugation at 13000 rpm for 10 min, the supernatants were removed. The pellets were washed twice with 70% ethanol, dried, added with water to dissolve, and then stored at −20° C.

The genomic DNA extracted from the transformant above was used as a template to perform PCR amplification reaction, using primer 1 and primer 4. PCR condition was as follows: 94° C. for 4 min; 30 cycles of 94° C. for 40 sec, 58° C. for 40 sec and 72° C. for 1 min, and 72° C. for 7 min, then 16° C. The PCR products were recovered by gel recovery kit and then sequenced. The sequencing results showed that the nucleotide sequence of PCR product was consistent with that of SEQ ID NO: 6. Thus, the *Trichoderma reesei* engineering strain carrying the fusion gene of cellulase SCD45-*Streptomyces* subtilisin inhibitor (SSI) were constructed, and named *Trichoderma reesei* PS.

As a control, the *Trichoderma reesei* engineering strain carrying the gene of cellulase SCD45 was constructed using the same method as mentioned above, and named *Trichoderma reesei* SCD45.

1.4 Fermentation Process of Shake Flask and Determination of Enzymatic Activity.

The *Trichoderma reesei* host cell, the *Trichoderma reesei* recombinant strain SCD45 and *Trichoderma reesei* PS were inoculated respectively on PDA plates and cultured at 30° C. for 1 day. After the spores were abundant, two pieces of mycelium with diameter of 1 cm were transferred into 250 mL flasks containing 50 mL of fermentation medium (1.5% glucose, 1.7% lactose, 2.5% corn pulp, 0.44% $(NH_4)_2SO_4$, 0.09% $MgSO_4$, 2% $KH_2PO_4$, 0.04% $CaCl_2$, 0.018% Tween-80, 0.018% trace elements) and cultured at 30° C. for 48 hours. Then after culture at 25° C. for another 48 hours, the fermentation supernatant was used for SDS-PAGE electrophoresis and the determination of enzymatic activity of cellulase.

(1) Method for Determining Enzymatic Activity

One unit of enzymatic activity is the amount of the enzyme required to degrade and release 1 μmol of reducing-end per minute from 1% CMC-Na solution at a condition of pH 6.0 and 50° C.

0.5 ml of diluted enzyme solutions was added to individual test tubes and put the tubes into a water bath at 50±0.1° C. for 2 min for preheating. 0.5 mL of substrate solutions was added to the sample tubes accurately. After accurate 15 minutes, 0.2 ml of sodium carbonate solution was added to each tube quickly and 0.5 ml of substrate solution was added into the blank tube and mixed well. The blank tube was used for zero setting, and the absorbance was measured at a wavelength of 410 nm with a spectrophotometer.

$$\text{Enzymatic activity } X = A \times 1 \div 0.5 \times n \div 15$$

Wherein, X—Unit of enzymatic activity, IU/g (mL);

A—Content of p-nitrophenol calculated from the absorbance on the standard curve, μmol;

1/0.5—Volume of the enzyme solution added

15—Reaction time of the test solution with the substrate n—Dilution factors (2) Results The results of the SDS-PAGE electrophoresis are shown in FIG. 1, in which the protein bands indicated by arrows pointed in Lane 1 and Lane 2 are the fusion protein recombinantly expressed by *Trichoderma reesei* PS, and have a molecular weight significantly higher than that of cellulase SCD45 indicated by arrows pointed in Lane 3 and Lane 4, and basically consistent with the theoretical molecular weight of the fusion protein. The results illustrate that the *Trichoderma reesei* recombinant strain PS constructed in the present disclosure can effectively express the fusion protein of cellulase SCD45-*Streptomyces* subtilisin inhibitor (SSI), and further illustrate that the fusion polynucleotide sequence of the cellulase gene and the *Streptomyces* subtilisin inhibitor (SSI) gene encodes a protein in which cellulase and the protease inhibitory peptide are fused together in a covalent manner to perform their functions.

The results of enzymatic activity determination show that the enzymatic activity in the fermentation supernatant of the host cells is only 4.5 U/ml, while that of *Trichoderma reesei* SCD45 and *Trichoderma reesei* PS are 117 U/mL and 109 U/mL, respectively. Thus, the *Trichoderma reesei* recombinant strain SCD45 constructed in the present disclosure can efficiently express cellulase SCD45 and *Trichoderma reesei* PS can efficiently express the fusion protein of cellulase SCD45-*Streptomyces* subtilisin inhibitor (SSI). Meanwhile the enzymatic activities of cellulase are not affected.

1.5 Fermentation Process

The *Trichoderma reesei* recombinant strain SCD45 and *Trichoderma reesei* PS were inoculated on PDA plates and cultured at 30° C. for 5 days. The fresh spores from the PDA plates were transferred to a 3 L shaking flask containing 1 L of liquid fermentation medium (the formulation of the liquid fermentation medium: 1% glucose, 1.5% corn pulp, 0.05% calcium chloride, 0.9% ammonium sulfate, 0.2% magnesium sulfate heptahydrate, 2% potassium dihydrogen phosphate, 0.02% Tween-80, 0.02% polypropylene glycol, and 0.02% inorganic salt solution, pH 5.5, wherein the inorganic salt solution was composed of 5 g/L $FeSO_4 \cdot 7H_2O$, 1.6 g/L $MnSO_4 \cdot H_2O$ and 1.2 g/L $ZnSO_4$ 7 $H_2O$) and cultured at 30° C. for 1 day with shaking at 220 rpm.

The fermentation broth in the shake flask was transferred to a 20 L fermentor containing 10 L of the above fermentation medium (pH 5.5). The temperature was controlled at 28±1° C. and the pH was 5.0±0.2. After 165 hours of fermentation, the fermentation broth was collected and filtered for further measurement and analysis of enzymatic activities.

The enzymatic activity of cellulase in the fermentation supernatant was determined by the method mentioned in Example 1.4. The results show that the enzymatic activity of cellulase in the supernatants of *Trichoderma reesei* SCD45 and *Trichoderma reesei* PS are 1980 U/mL and 1865 U/mL, respectively. The results further showed that the *Trichoderma reesei* recombinant strain SCD45 can effectively express cellulase SCD45 and the *Trichoderma reesei* recombinant strain PS can effectively express the fusion protein of cellulase SCD45-*Streptomyces* subtilisin inhibitor (SSI).

1.6 Protease Resistance of Cellulase

Firstly, the fermentation supernatants of *Trichoderma reesei* SCD45 and *Trichoderma reesei* PS were diluted with acetic acid buffer (pH 7.5) to 600 U/ml respectively. Then, 8 ml of the diluted fermentation supernatants and 1 ml of protease with pH of 10.5 and protease enzymatic activity of 120000 U/ml were mixed well to obtain a mixed enzyme solution, which was placed at room temperature for 12 h and then 40° C. for 24 h. After that, the enzymatic activities of cellulase were detected respectively. The initial enzymatic activity in the mixed solution was set as 100%, and the residual enzymatic activities of cellulase were calculated. The specific results are shown in Table 1.

TABLE 1

| | Residual enzymatic activities of cellulase | |
|---|---|---|
| Cellulase | Room temperature for 12 h | 40° C. for 24 h |
| Cellulase SCD45 | 91.4% | 8.1% |
| Fusion protein of cellulase SCD45-SSI | 99.7% | 74.0% |

As shown in Table 1, in the presence of protease, after being placed at room temperature for 12 h, the residual enzymatic activity of cellulase SCD45 expressed by *Trichoderma reesei* SCD45 is 91.4%, while that of the fusion protein of cellulase SCD45-*Streptomyces* subtilisin inhibitor (SSI) expressed by *Trichoderma reesei* PS is 99.7%; after being placed at 40° C. for 24 h, the residual enzymatic activity of cellulase SCD45 is only 8.1%, while that of the fusion protein of cellulase SCD45-protease inhibitory peptide is 74.0%, which had been significantly improved.

The above results show that through the fusion expression of cellulase and the *Streptomyces* subtilisin inhibitor (SSI), the protease resistance of cellulase can be significantly improved and the degradation of cellulase by protease can be effectively reduced, achieving unexpected technical effects. The cellulase with protease resistance provided by the present disclosure is more suitable for use in detergent field.

1.7 Stability of Cellulase in Laundry Detergent

The fermentation supernatants of *Trichoderma reesei* SCD45 and *Trichoderma reesei* PS were diluted to 1000 U/ml with acetic acid buffer (pH 7.5), respectively. 2 ml of the diluted fermentation supernatants, 0.06 ml protease (pH 10.5, protease enzymatic activity 480000 U/ml) and 18 ml of White Cat detergent base were mixed well to obtain an enzyme-containing detergent, which was placed at 37° C. for 24 h, 48 h and 72 h. After that, the enzymatic activity of cellulase was detected using the method described in Example 3. The initial enzymatic activity in the enzyme-containing detergent was set as 100%, and the residual enzymatic activities of cellulase were calculated. The results are shown in Table 2.

TABLE 2

Residual enzymatic activities of cellulase in the enzyme-containing detergent at 37° C.

| Type of Cellulase | 24 h | 48 h | 72 h |
|---|---|---|---|
| Cellulase SCD45 | 12.1% | 2.1% | 0.9% |
| Fusion protein of cellulase SCD45-SSI | 59.5% | 28.9% | 14.2% |

As shown in Table 2, the residual enzymatic activities of cellulase in the enzyme-containing detergent added with the fusion protein of cellulase SCD45-*Streptomyces* subtilisin inhibitor (SSI) are significantly higher than that in the enzyme-containing detergent added with cellulase SCD45 after being placed at 37° C. for 24 h, 48 h and 72 h. The above results show that through the fusion expression of cellulase and protease inhibitory peptide, the present disclosure provides a cellulase with protease resistance, which can be wildly used in detergents to increase the stability of enzyme in detergent, and achieves unexpected technical effects.

Example 2 Improve Protease Resistance by Expressing Fusion Protein of Cellulase HGD45 and Protease Inhibitory Peptide PCL 2.1 Generation and Expression of the Fusion Gene of Cellulase HGD45-Protease Inhibitory Peptide PCL The applicant fused the gene of cellulase HGD45 with the gene of barley-derived protease inhibitory peptide PCL, to generate the fusion gene of cellulase HGD45-protease inhibitory peptide PCL.

The amino acid sequence of cellulase HGD45 is shown as SEQ ID NO: 11, and the encoding polynucleotide sequence thereof is shown as SEQ ID NO: 12.

The amino acid sequence of barley-derived protease inhibitory peptide PCL is shown as SEQ ID NO: 13, and the encoding polynucleotide sequence thereof is shown as SEQ ID NO: 14.

The gene of cellulase HGD45 and the gene of protease inhibitory peptide PCL were separately synthesized by Suzhou Genewiz Biotechnology Co., Ltd.

The specific procedures were as follows:

The gene fragment encoding cellulase HGD45 was amplified by PCR reaction with cellulase HGD45 gene as a template using primer 5 (shown as SEQ ID NO: 17) and primer 6 (shown as SEQ ID NO: 18).

The gene fragment encoding protease inhibitory peptide PCL was amplified by PCR reaction with protease inhibitory peptide PCL gene as a template using primer 7 (shown as SEQ ID NO: 19) and primer 8 (shown as SEQ ID NO: 20).

The U-Clone fragments of cellulase HGD45 and the U-Clone fragments of protease inhibitory peptide PCL were mixed in equal molar ratio. The fusion gene of cellulase HGD45-protease inhibitory peptide PCL was generated by PCR amplification reaction with the above U-Clone fragment mixture as a template using primer 5 and primer 8, and was named HGD45-PCL. The fusion gene comprises a polynucleotide sequence shown as SEQ ID NO: 16 and codes an amino acid sequence shown as SEQ ID NO: 15, in which the protease inhibitory peptide PCL was fused to the C-terminus of cellulase HGD45. The PCR reaction was carried out for 30 cycles of 94° C. for 40 seconds, 62° C. for 40 seconds, and 72° C. for 1 minute. After the final extension at 72° C. for 5 min, the products were stored at 16° C.

The HGD45-PCL fusion gene fragment was cloned into the *Trichoderma* expression plasmid pSC2G after double digestion with Xba I and Mlu I by using the U-Clone kit to construct the recombinant expression plasmid named HGD45-PCL-pSC2G. To ensure accuracy, several clones were sequenced for verification.

The recombinant expression plasmid with cellulase HGD45 gene was constructed by the same method as mentioned above and named HGD45-pSC2G.

The recombinant *Trichoderma reesei* engineering strain expressing the fusion protein of cellulase HGD45-protease inhibitory peptide PCL was constructed by the same method as mentioned in Example 1.3, and was named *Trichoderma reesei* HGD45-PCL.

As a control, the recombinant *Trichoderma reesei* engineering strain expressing cellulase HGD45 was also constructed, and was named *Trichoderma reesei* HGD45.

The fermentation was carried out by the same methods as mentioned in Examples 1.4 and 1.5, and the enzymatic activity of cellulase in the fermentation supernatant was determined.

2.2 Protease Resistance of Cellulase

The fermentation supernatants of *Trichoderma reesei* HGD45 and *Trichoderma reesei* HGD45-PCL were diluted to 1000 U/ml with acetic acid buffer (pH 7.5), respectively. 2 ml of the diluted fermentation supernatants, 0.06 ml protease (pH 10.5, protease enzymatic activity 480000 U/ml) and 18 ml of White Cat detergent base were mixed well to obtain an enzyme-containing detergent, which was placed at 37° C. for 48 h, 96 h, and 168 h. After that, the enzymatic activity of cellulase was detected. The initial enzymatic activity in the enzyme-containing detergent was set as 100%, and the residual enzymatic activities of cellulase were calculated. The results are shown in Table 3.

TABLE 3

Residual enzymatic activities of cellulase in the enzyme-containing detergent at 37° C.

| Type of Cellulase | 48 h | 96 h | 168 h |
|---|---|---|---|
| Cellulase HGD45 | 45.9% | 28.8% | 20.6% |
| Fusion protein of cellulase HGD45-PCL | 74.9% | 65.2% | 49.0% |

As shown in Table 3, the residual enzymatic activities of cellulase in the enzyme-containing detergent added with the fusion protein of cellulase HGD45-protease inhibitory peptide PCL are significantly higher than that in the enzyme-containing detergent added with cellulase HGD45 after being placed at 37° C. for 48 h, 96 h and 168 h. The above results show that through the fusion expression of cellulase HGD45 and protease inhibitory peptide PCL, the present disclosure significantly improves the resistance of cellulose and the stability of cellulase in detergents, achieving unexpected technical effects.

Example 3 Improve Protease Resistance by Expressing Fusion Protein of Cellulase NT45 and Marinostatin (MST)

3.1 Generation and Expression of the Fusion Gene of Cellulase NT45-Marinostatin (MST)

The applicant fused the gene of cellulase NT45 with the gene of *Alteromonas*-derived marinostatin (MST), to generate the fusion gene of cellulase NT45-marinostatin (MST).

The amino acid sequence of cellulase NT45 is shown as SEQ ID NO: 21, and the encoding polynucleotide sequence thereof is shown as SEQ ID NO: 22.

The amino acid sequence of marinostatin (MST) is shown as SEQ ID NO: 23, and the encoding polynucleotide sequence thereof is shown as SEQ ID NO: 24.

The gene of cellulase NT45 and the gene of marinostatin (MST) were separately synthesized by Suzhou Genewiz Biotechnology Co., Ltd.

The specific procedures were as follows:

The gene fragment encoding cellulase NT45 was amplified by PCR reaction with cellulase NT45 gene as a template using primer 9 (shown as SEQ ID NO: 27) and primer 10 (shown as SEQ ID NO: 28).

The gene fragment encoding marinostatin (MST) was amplified by PCR reaction with marinostatin (MST) gene as a template using primer 11 (shown as SEQ ID NO: 29) and primer 12 (shown as SEQ ID NO: 30).

The U-Clone fragments of marinostatin (MST) and the U-Clone fragments of cellulase NT45 were mixed in equal molar ratio. The fusion gene of cellulase NT45-marinostatin (MST) was generated by PCR amplification reaction with the above U-Clone fragment mixture as a template using primer 9 and primer 12, and was named NT45-MST. The fusion gene comprises a polynucleotide sequence shown as SEQ ID NO: 26 and codes an amino acid sequence shown as SEQ ID NO: 25, in which the marinostatin (MST) was fused to the C-terminus of cellulase NT45. The PCR reaction was carried out for 30 cycles of 94° C. for 40 seconds, 62° C. for 40 seconds, and 72° C. for 1 minute. After the final extension at 72° C. for 5 min, the products were stored at 16° C.

The NT45-MST fusion gene fragment was cloned into the *Trichoderma* expression plasmid pSC2G after double digestion with Xba I and Mlu I by using the U-Clone kit to construct the recombinant expression plasmid named NT45-MST-pSC2G. To ensure accuracy, several clones were sequenced for verification.

The recombinant expression plasmid with cellulase NT45 gene was constructed by the same method as mentioned above and named NT45-pSC2G.

The recombinant *Trichoderma reesei* engineering strain expressing the fusion protein of cellulase NT45-marinostatin (MST) was constructed by the same method as mentioned in Example 1.3, and was named *Trichoderma reesei* NT45-MST.

As a control, the recombinant *Trichoderma reesei* engineering strain expressing cellulase NT45 was also constructed, and was named *Trichoderma reesei* NT45.

The fermentation was carried out by the same methods as mentioned in Examples 1.4 and 1.5, and the enzymatic activity of cellulase in the fermentation supernatant was determined.

3.2 Protease Resistance of Cellulase

In the experimental group, the protease was diluted to 3000 U/ml with acetic acid buffer (pH 10.5). 133 μl of diluted protease solution and 67 μl of above fermentation supernatant (enzymatic activity of cellulase was 100 U/ml) were mixed well and placed at 37° C. for 3 days.

In the control group, 133 μl of acetic acid buffer (pH 10.5) and 67 μl of fermentation supernatant (enzymatic activity of cellulase was 100 U/ml) were mixed well and stored at 37° C. for 3 days.

The enzymatic activities of the cellulases in the experimental group and the control group were detected, respectively. The enzymatic activity in the control group was set as 100%, and the residual enzymatic activities of cellulase in the experimental group were calculated. The results are shown in Table 4.

TABLE 4

| Residual enzymatic activities of cellulase stored at 37° C. for 3 days | |
|---|---|
| Type of Cellulase | Residual enzymatic activity of cellulase |
| Cellulase NT45 | 77.3% |
| Fusion protein of cellulase NT45-MST | 85.9% |

As shown in Table 4, after storage at 37° C. for 3 days, the residual enzymatic activity of the fusion protein of cellulase NT45-marinostatin (MST) recombinantly expressed by *Trichoderma reesei* NT45-MST is 85.9%, significantly higher than that of cellulase NT45. The results show that the protease resistance of the fusion protein of cellulase NT45-marinostatin (MST) has been significantly improved.

Example 4 Improve Protease Resistance by Expressing Fusion Protein of Cellulase SCD45 and Pro-Peptide of Subtilisin (PPS)

4.1 Generation and Expression of the Fusion Gene of Propeptide PPS-Cellulase SCD45

The applicant fused the gene of cellulase SCD45 with the gene of *Bacillus* amyloliquefacien-derived propeptide PPS, to generate the fusion gene of propeptide PPS-cellulase SCD45.

The amino acid sequence of propeptide PPS is shown as SEQ ID NO: 31, and the encoding polynucleotide sequence thereof is shown as SEQ ID NO: 32.

The gene of propeptide PPS was synthesized by Suzhou Genewiz Biotechnology Co., Ltd.

The specific procedures were as follows:

The gene fragment encoding propeptide PPS was amplified by PCR reaction with propeptide PPS gene as a template using primer 13 (shown as SEQ ID NO: 35) and primer 14 (shown as SEQ ID NO: 36).

The gene fragment encoding cellulase SCD45 was amplified by PCR reaction with cellulase SCD45 gene as a template using primer 15 (shown as SEQ ID NO: 37) and primer 16 (shown as SEQ ID NO: 38).

The U-Clone fragments of purified propeptide PPS and the U-Clone fragments of cellulase SCD45 were mixed in equal molar ratio. The fusion gene of propeptide PPS-cellulase SCD45 was generated by PCR amplification reaction with the above U-Clone fragment mixture as a template using primer 13 and primer 16, and was named PPS-SCD45. The fusion gene comprises a polynucleotide sequence shown as SEQ ID NO: 34 and codes an amino acid sequence shown as SEQ ID NO: 33, in which the propeptide PPS was fused to the N-terminus of cellulase SCD45. The PCR reaction was carried out for 30 cycles of 94° C. for 40 seconds, 62° C. for 40 seconds, and 72° C. for 1 minute. After the final extension at 72° C. for 5 min, the products were stored at 16° C.

The PPS-SCD45 fusion gene fragment was cloned into the *Trichoderma* expression plasmid pSC2G after double digestion with Xba I and Mlu I by using the U-Clone kit to construct the recombinant expression plasmid named PPS-SCD45-pSC2G. To ensure accuracy, several clones were sequenced for verification.

The recombinant *Trichoderma reesei* engineering strain expressing the fusion protein of propeptide PPS-cellulase SCD45 was constructed by the same method as mentioned in Example 1.3, and was named *Trichoderma reesei* PPS-SCD45.

The recombinant *Trichoderma reesei* strain expressing cellulase SCD45 constructed as in Example 1.3 was used as a control.

The fermentation was carried out by the same methods as mentioned in Examples 1.4 and 1.5, and the enzymatic activity of cellulase in the fermentation supernatant was determined.

4.2 Protease Resistance of Cellulase

In the experimental group, the protease was diluted to 3000 U/ml with acetic acid buffer (pH 10.5). 133 µl of diluted protease solution and 67 µl of above fermentation supernatant (enzymatic activity of cellulase was 100 U/ml) of *Trichoderma reesei* strains were mixed well and placed at 37° C. for 3 days.

In the control group, 133 µl of acetic acid buffer (pH 10.5) and 67 µl of fermentation supernatant (enzymatic activity of cellulase was 100 U/ml) of *Trichoderma reesei* strains were mixed well and stored at 37° C. for 3 days.

The enzymatic activities of the cellulase in the experimental group and the control group were detected, respectively. The enzymatic activity in the control group was set as 100%, and the residual enzymatic activities of cellulase in the experimental group were calculated. The results are shown in Table 5.

TABLE 5

Residual enzymatic activities of cellulase stored at 37° C. for 3 days

| Type of Cellulase | Residual enzymatic activity of cellulase |
|---|---|
| Cellulase SCD45 | 79.4% |
| Fusion protein of PPS- SCD45 | 88.8% |

As shown in Table 5, after storage at 37° C. for 3 days in the presence of protease, the residual enzymatic activity of the fusion protein of propeptide PPS-cellulase SCD45 recombinantly expressed by *Trichoderma reesei* PPS-SCD45 is 88.8%, significantly higher than that of cellulase SCD45. The protease resistance had been significantly improved.

Example 5 Improve Protease Resistance by Expressing Fusion Protein of Lipase and *Streptomyces* Subtilisin Inhibitor (SSI)

In addition to cellulase, the method provided in the present disclosure can be suitable for use in lipase to improve significantly the protease resistance.

5.1 Generation and Expression of the Fusion Gene of Lipase TG-*Streptomyces* Subtilisin Inhibitor (SSI)

The applicant fused the gene of lipase TG with the gene of *Streptomyces* subtilisin inhibitor (SSI), to generate the fusion gene of lipase TG-*Streptomyces* subtilisin inhibitor (SSI).

The amino acid sequence of lipase TG is shown as SEQ ID NO: 39, and the encoding polynucleotide sequence thereof is shown as SEQ ID NO: 40.

The gene of lipase TG was synthesized by Suzhou Genewiz Biotechnology Co., Ltd.

The specific procedures were as follows:

The gene fragment encoding lipase TG was amplified by PCR reaction with lipase TG gene as a template using primer 17 (shown as SEQ ID NO: 43) and primer 18 (shown as SEQ ID NO: 44).

The gene fragment encoding *Streptomyces* subtilisin inhibitor (SSI) was amplified by PCR reaction with *Streptomyces* subtilisin inhibitor (SSI) gene as a template using primer 19 (shown as SEQ ID NO: 45) and primer 4 (shown as SEQ ID NO: 10) described in Example 1.1.

The U-Clone fragments of *Streptomyces* subtilisin inhibitor (SSI) and the U-Clone fragments of lipase TG were mixed in equal molar ratio. The fusion gene of lipase TG-*Streptomyces* subtilisin inhibitor (SSI) was generated by PCR amplification reaction with the above U-Clone fragment mixture as a template using primer 17 and primer 4 described in Example 1.1, and was named TG-SSI. The fusion gene comprises a polynucleotide sequence shown as SEQ ID NO: 42 and codes an amino acid sequence shown as SEQ ID NO: 41, in which the *Streptomyces* subtilisin inhibitor (SSI) was fused to the C-terminus of lipase TG. The PCR reaction was carried out for 30 cycles of 94° C. for 40 seconds, 62° C. for 40 seconds, and 72° C. for 1 minute. After the final extension at 72° C. for 5 min, the products were stored at 16° C.

The TG-SSI fusion gene fragment was cloned into the *Trichoderma* expression plasmid pSC2G after double digestion with Xba I and Mlu I by using the U-Clone kit to construct the recombinant expression plasmid named TG-SSI-pSC2G. To ensure accuracy, several clones were sequenced for verification.

The recombinant expression plasmid with lipase TG gene was constructed by the same method as mentioned above and named TG-pSC2G.

The recombinant *Trichoderma reesei* engineering strain expressing the fusion protein of lipase TG-*Streptomyces* subtilisin inhibitor (SSI) was constructed by the same method as mentioned in Example 1.3, and was named *Trichoderma reesei* TGS.

As a control, the recombinant *Trichoderma reesei* engineering strain expressing lipase TG was also constructed, and was named *Trichoderma reesei* TG.

The fermentation was carried out by the same methods as mentioned in Examples 1.4 and 1.5, and the enzymatic activity of cellulase in the fermentation supernatant was determined.

5.2 Protease Resistance of Lipase

The fermentation supernatants of *Trichoderma reesei* TG and *Trichoderma reesei* TGS were diluted with acetic acid buffer (pH 7.5) to 3000 U/ml respectively. Then, 9 ml of the diluted fermentation supernatants and 1 ml of protease with pH of 10.5 and protease enzymatic activity of 5000 U/ml were mixed well to obtain a mixed enzyme solution, which was placed at 37° C. for a week, and samples were taken at 2d, 5d, and 6d for lipase enzymatic activity detection. The initial enzymatic activity in the mixed enzyme solution was set as 100%, and the residual enzymatic activities of lipase were calculated. The specific results are shown in Table 6.

TABLE 6

Residual enzymatic activities of lipase at 37° C.

| Type of Lipase | 2 d | 5 d | 6 d |
|---|---|---|---|
| Lipase TG | 78.5% | 50.1% | 34.6% |
| Fusion protein of lipase TG-SSI | 105.7% | 76.2% | 64.6% |

As shown in Table 6, after being placed at 37° C. for 2 days, 5 days and 6 days in the presence of protease, compared with lipase TG, the residual enzymatic activity of the fusion protein of lipase TG-*Streptomyces* subtilisin inhibitor (SSI) is significantly improved. Especially, the residual enzymatic activity of the fusion protein is 64.6%, which is 86.7% higher than that of lipase TG and has been significantly improved.

The above results show that through the fusion expression of lipase and the protease inhibitory peptide, the protease resistance of lipase can be significantly improved and the degradation of lipase by protease can be effectively reduced, which achieved unexpected technical effects. The lipase with protease resistance provided by the present disclosure is more suitable for use in detergent field.

In addition to cellulase and lipase, the method provided by the present disclosure can be suitable for use in other laundry enzymes, such as cutinase, amylase, pectinase, mannanase, arabinase, galactosidase, xylanase, laccase and peroxidase, etc., to significantly improve the protease resistance of these enzymes to reduce the degradation effect of the protease on them, and achieve coexistence of above-mentioned enzymes and protease in the detergent.

The method described in the present disclosure is not limited to the fusion expression of the laundry enzyme with *Streptomyces* subtilisin inhibitor (SSI), protease inhibitory peptide PCL, marinostatin (MST) or propeptide PPS, but also with protease inhibitory peptide Bowman-Birk or the propeptide derived from *Bacillus* sp., to enhance the protease resistance of the laundry enzymes. Moreover, the method described in the present disclosure is not limited to the fusion expression of the laundry enzyme with a single protease inhibitory peptide, but also with two or three protease inhibitory peptides to enhance the protease resistance of laundry enzymes. "Fusion" described herein may be the fusion of protease inhibitory peptide to the N-terminus, C-terminus or interior of the laundry enzyme.

The method for producing laundry enzyme with protease resistance provided by the present disclosure is described in detail. The principle and embodiment of the present disclosure have been described with reference to specific examples, and the description of the above embodiment is merely illustrative of the method and the core idea of the present disclosure. It should be noted that for those skilled in the art, without departing from the principle of the present disclosure, several improvements and modifications can be made to the present disclosure, and these improvements and modifications also fall within the protection scope of the claims of the present disclosure.

The invention claimed is:

1. A laundry enzyme with protease resistance, which is a fusion protein of a laundry enzyme and a protease inhibitory peptide; wherein the laundry enzyme is selected from the group consisting of cellulase, lipase, cutinase, amylase, glucoamylase, pectinase, mannanase, arabinase, galactosidase, xylanase, laccase and peroxidase; and the protease inhibitory peptide is selected from the group consisting of *Streptomyces* subtilisin inhibitor (SSI) from *Streptomyces* sp., protease inhibitory peptide PCL from Barley, protease inhibitor marinostatin (MST) from *Alteromonas*, and a mixture thereof.

2. The laundry enzyme with protease resistance according to claim 1, wherein the laundry enzyme and the protease inhibitory peptide of the fusion protein are fused covalently.

3. The laundry enzyme with protease resistance according to claim 1, wherein the laundry enzyme is cellulase or lipase, and the protease inhibitory peptide is selected from the group consisting of *Streptomyces* subtilisin inhibitor (SSI) from *Streptomyces* sp., protease inhibitory peptide PCL from Barley, and protease inhibitor marinostatin (MST) from *Alteromonas*.

4. The laundry enzyme with protease resistance according to claim 3, wherein the laundry enzyme is cellulase, and the protease inhibitory peptide is selected from the group consisting of protease inhibitory peptide PCL from Barley, and protease inhibitor marinostatin (MST) from *Alteromonas*.

5. The laundry enzyme with protease resistance according to claim 1, wherein the laundry enzyme is cellulase.

6. The laundry enzyme with protease resistance according to claim 1, wherein the laundry enzyme is lipase.

7. The laundry enzyme with protease resistance according to claim 1, wherein the protease inhibitory peptide is fused to the laundry enzyme in N-terminus, C-terminus or middle.

* * * * *

SEQUENCE LISTING

```
<160> NUMBER OF SEQ ID NOS: 45

<210> SEQ ID NO 1
<211> LENGTH: 288
<212> TYPE: PRT
<213> ORGANISM: Artificial
<220> FEATURE:
<223> OTHER INFORMATION: Amino acid sequence of cellulase SCD45

<400> SEQUENCE: 1

Met Arg Ser Ser Pro Leu Leu Pro Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Ser Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asn Phe Ser Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125
```

```
Ser Thr Ser Thr Gly Gly Asp Leu Gly Ser Asn His Phe Asp Leu Asn
    130                 135                 140
Ile Pro Gly Gly Val Gly Ile Phe Asp Gly Cys Thr Pro Gln Phe
145                 150                 155                 160
Gly Gly Leu Pro Gly Gln Arg Tyr Gly Gly Ile Ser Ser Arg Asn Glu
                165                 170                 175
Cys Asp Ser Phe Pro Asp Ala Leu Lys Pro Gly Cys Tyr Trp Arg Phe
                180                 185                 190
Asp Trp Phe Lys Asn Ala Asp Asn Pro Ser Phe Ser Phe Arg Gln Val
                195                 200                 205
Gln Cys Pro Ala Glu Leu Val Ala Arg Thr Gly Cys Arg Arg Asn Asp
    210                 215                 220
Asp Gly Asn Phe Pro Ala Val Gln Ile Pro Ser Ser Thr Ser Ser
225                 230                 235                 240
Ser Pro Pro Val Gln Pro Thr Thr Pro Ser Gly Cys Thr Ala Glu Arg
                245                 250                 255
Trp Ala Gln Cys Gly Gly Asn Gly Trp Ser Gly Cys Thr Thr Cys Val
                260                 265                 270
Ala Gly Ser Thr Cys Thr Lys Ile Asn Asp Trp Tyr His Gln Cys Leu
    275                 280                 285

<210> SEQ ID NO 2
<211> LENGTH: 867
<212> TYPE: DNA
<213> ORGANISM: Artificial
<220> FEATURE:
<223> OTHER INFORMATION: Polynucleotide sequence of cellulase SCD45

<400> SEQUENCE: 2
atgcgttcct ccccctcct cccgtccgcc gttgtggccg ccctgccggt gttggccctt    60
gccgctgatg gcaggtccac cgctactggg gactgctgca agccttcgtg cggctgggcc   120
aagaaggctg gcgtgaacca gcctgtcttt tcctgcaacg ccaacttcca gcgtatcacg   180
gacttcgacg ccaagtccgg ctgcgagccg ggcggtgtcg cctactcgtg cgccgaccag   240
accccatggg ctgtgaacga caacttcagc ctcggttttg ctgccaccto tattgccggc   300 agcaatgagg cgggctggtg ctgcgcctgc tacgagctca ccttcacatc cggtcctgtt   360
gctggcaaga gatggtcgt ccagtccacc agcactggcg tgatcttgg cagcaaccac   420 ttcgatctca acatccccgg cggcggcgtc ggcatcttcg acggatgcac tccccagttc   480
ggcggtctgc ccggccagcg ctacggcgg atctcgtccc gcaacgagtg cgatagcttc   540
cccgacgccc tcaagcccgg ctgctactgg cgcttcgact ggttcaagaa cgccgacaat   600
ccgagcttca gcttccgtca ggtccagtgc cagccgagc tcgtcgctcg caccggatgc   660
cgccgcaacg acgacggcaa cttccctgcc gtccagatcc cctccagcag caccagctct   720
agcccgccag tccagcctac gactcccagc ggctgcactg ctgagaggtg ggctcagtgc   780
ggcggcaatg gctggagcgg ctgcaccacc tgcgtcgctg gcagcacttg cacgaagatt   840
aatgactggt atcatcagtg cctgtag                                      867

<210> SEQ ID NO 3
<211> LENGTH: 116
<212> TYPE: PRT
<213> ORGANISM: Artificial
<220> FEATURE:
<223> OTHER INFORMATION: Amino acid sequence of Streptomyces subtilisin
      inhibitor (SSI)
```

<400> SEQUENCE: 3

Ala Pro Gly Asp Ala Pro Ser Ala Leu Tyr Ala Pro Ser Ala Leu Val
1               5                   10                  15

Leu Thr Val Gly Lys Gly Val Ser Ala Thr Ala Ala Pro Glu Arg
            20                  25                  30

Ala Val Thr Leu Thr Cys Ala Pro Gly Pro Ser Gly Thr His Pro Ala
            35                  40                  45

Ala Gly Ser Ala Cys Ala Asp Leu Ala Ala Val Gly Gly Asp Leu Asn
        50                  55                  60

Lys Ile Thr Arg Gly Glu Asp Val Met Cys Pro Pro Val Tyr Asp Pro
65                  70                  75                  80

Val Leu Leu Thr Val Cys Gly Val Trp Gln Gly Lys Arg Val Ser Tyr
                85                  90                  95

Glu Arg Val Phe Glu Asn Glu Cys Glu Met Asn Ala His Gly Ser Ser
                100                 105                 110

Val Phe Ala Phe
        115

<210> SEQ ID NO 4
<211> LENGTH: 348
<212> TYPE: DNA
<213> ORGANISM: Artificial
<220> FEATURE:
<223> OTHER INFORMATION: Polynucleotide sequence of Streptomyces
      subtilisin inhibitor (SSI)

<400> SEQUENCE: 4
gccccgggcg atgccccgag cgccctctac gcccctagcg ccctcgtcct caccgtcgga      60
aagggcgtca gcgccacgac cgccgccccg gagcgcgccg tcaccctcac ttgtgccccg     120
ggcccgagcg gcacccaccc ggccgccggc agcgcttgtg ccgacctcgc cgccgtcggc     180
ggcgacctca acaagattac cgcggcgag gacgtcatgt gtccgccggt ctacgacccg      240
gtcctcctca ccgtctgtgg cgtctggcaa ggtaagcgcg tcagctacga gcgcgtgttc     300
gagaacgagt gcgagatgaa cgcccacggc agcagcgtct tcgctttc                  348

<210> SEQ ID NO 5
<211> LENGTH: 383
<212> TYPE: PRT
<213> ORGANISM: Artificial
<220> FEATURE:
<223> OTHER INFORMATION: Amino acid sequence of fusion protein

<400> SEQUENCE: 5

Ala Asp Gly Arg Ser Thr Arg Tyr Trp Asp Cys Cys Lys Pro Ser Cys
1               5                   10                  15

Gly Trp Ala Lys Lys Ala Ser Val Asn Gln Pro Val Phe Ser Cys Asn
            20                  25                  30

Ala Asn Phe Gln Arg Ile Thr Asp Phe Asp Ala Lys Ser Gly Cys Glu
            35                  40                  45

Pro Gly Gly Val Ala Tyr Ser Cys Ala Asp Gln Thr Pro Trp Ala Val
        50                  55                  60

Asn Asp Asn Phe Ser Leu Gly Phe Ala Ala Thr Ser Ile Ala Gly Ser
65                  70                  75                  80

Asn Glu Ala Gly Trp Cys Cys Ala Cys Tyr Glu Leu Thr Phe Thr Ser
                85                  90                  95

Gly Pro Val Ala Gly Lys Lys Met Val Val Gln Ser Thr Ser Thr Gly
                100                 105                 110

Gly Asp Leu Gly Ser Asn His Phe Asp Leu Asn Ile Pro Gly Gly Gly
            115                 120                 125

Val Gly Ile Phe Asp Gly Cys Thr Pro Gln Phe Gly Gly Leu Pro Gly
        130                 135                 140

Gln Arg Tyr Gly Gly Ile Ser Ser Arg Asn Glu Cys Asp Ser Phe Pro
145                 150                 155                 160

Asp Ala Leu Lys Pro Gly Cys Tyr Trp Arg Phe Asp Trp Phe Lys Asn
                165                 170                 175

Ala Asp Asn Pro Ser Phe Ser Phe Arg Gln Val Gln Cys Pro Ala Glu
            180                 185                 190

Leu Val Ala Arg Thr Gly Cys Arg Arg Asn Asp Asp Gly Asn Phe Pro
        195                 200                 205

Ala Val Gln Ile Pro Ser Ser Ser Thr Ser Ser Ser Pro Pro Val Gln
    210                 215                 220

Pro Thr Thr Pro Ser Gly Cys Thr Ala Glu Arg Trp Ala Gln Cys Gly
225                 230                 235                 240

Gly Asn Gly Trp Ser Gly Cys Thr Thr Cys Val Ala Gly Ser Thr Cys
                245                 250                 255

Thr Lys Ile Asn Asp Trp Tyr His Gln Cys Leu Ala Pro Gly Asp Ala
            260                 265                 270

Pro Ser Ala Leu Tyr Ala Pro Ser Ala Leu Val Leu Thr Val Gly Lys
        275                 280                 285

Gly Val Ser Ala Thr Thr Ala Ala Pro Glu Arg Ala Val Thr Leu Thr
    290                 295                 300

Cys Ala Pro Gly Pro Ser Gly Thr His Pro Ala Ala Gly Ser Ala Cys
305                 310                 315                 320

Ala Asp Leu Ala Ala Val Gly Gly Asp Leu Asn Lys Ile Thr Arg Gly
                325                 330                 335

Glu Asp Val Met Cys Pro Pro Val Tyr Asp Pro Val Leu Leu Thr Val
            340                 345                 350

Cys Gly Val Trp Gln Gly Lys Arg Val Ser Tyr Glu Arg Val Phe Glu
        355                 360                 365

Asn Glu Cys Glu Met Asn Ala His Gly Ser Ser Val Phe Ala Phe
    370                 375                 380

<210> SEQ ID NO 6
<211> LENGTH: 1149
<212> TYPE: DNA
<213> ORGANISM: Artificial
<220> FEATURE:
<223> OTHER INFORMATION: Polynucleotide sequence of fusion gene

<400> SEQUENCE: 6
gctgatggca ggtccacccg ctactgggac tgctgcaagc cttcgtgcgg ctgggccaag      60
aaggctggcg tgaaccagcc tgtctttccc tgcaacgcca acttccagcg tatcacggac     120
ttcgacgcca agtccggctg cgagccgggc ggtgtcgcct actcgtgcgc cgaccagacc     180
ccatgggctg tgaacgacaa cttcagcctc ggttttgctg ccacctctat tgccggcagc     240
aatgaggcgg gctggtgctg cgcctgctac gagctcacct tcacatccgg tcctgttgct     300
ggcaagaaga tggtcgtcca gtccaccagc actggcggtg atcttggcag caaccacttc     360
gatctcaaca tccccggcgg cggcgtcggc atcttcgacg gatgcactcc ccagttcggc     420
ggtctgcccg gccagcgcta cggcggcatc tcgtcccgca acgagtgcga tagcttcccc     480
gacgccctca gcccggctg ctactggcgc ttcgactggt tcaagaacgc cgacaatccg     540

-continued

```
agcttcagct tccgtcaggt ccagtgccca gccgagctcg tcgctcgcac cggatgccgc    600
cgcaacgacg acggcaactt ccctgccgtc cagatcccct ccagcagcac cagctctagc    660
ccgccagtcc agcctacgac tcccagcggc tgcactgctg agaggtgggc tcagtgcggc    720
ggcaatggct ggagcggctg caccacctgc gtcgctggca gcacttgcac gaagattaat    780
gactggtatc atcagtgcct ggccccgggc gatgccccga gcgccctcta cgccccuagc    840
gccctcgtcc tcaccgtcgg aaagggcgtc agcgccacga ccgccgcccc ggagcgcgcc    900
gtcaccctca cttgtgcccc gggcccgagc ggcacccacc cggccgccgg cagcgcttgt    960
gccgacctcg ccgccgtcgg cggcgacctc aacaagatta cccgcggcga ggacgtcatg   1020
tgtccgccgg tctacgaccc ggtcctcctc accgtctgtg gcgtctggca aggtaagcgc   1080
gtcagctacg agcgcgtgtt cgagaacgag tgcgagatga acgcccacgg cagcagcgtc   1140
ttcgctttc                                                            1149

<210> SEQ ID NO 7
<211> LENGTH: 45
<212> TYPE: DNA
<213> ORGANISM: Artificial
<220> FEATURE:
<223> OTHER INFORMATION: Primer

<400> SEQUENCE: 7
ctagtgtgcc tctagaggag cgggctgatg gcaggtccac ccgct                      45

<210> SEQ ID NO 8
<211> LENGTH: 39
<212> TYPE: DNA
<213> ORGANISM: Artificial
<220> FEATURE:
<223> OTHER INFORMATION: Primer

<400> SEQUENCE: 8
ctcggggcat cgcccggggc caggcactga tgataccag                             39

<210> SEQ ID NO 9
<211> LENGTH: 39
<212> TYPE: DNA
<213> ORGANISM: Artificial
<220> FEATURE:
<223> OTHER INFORMATION: Primer

<400> SEQUENCE: 9
ctggtatcat cagtgcctgg ccccgggcga tgccccgag                             39

<210> SEQ ID NO 10
<211> LENGTH: 36
<212> TYPE: DNA
<213> ORGANISM: Artificial
<220> FEATURE:
<223> OTHER INFORMATION: Primer

<400> SEQUENCE: 10
tcgccacgga gctttactag aaagcgaaga cgctgc                                36

<210> SEQ ID NO 11
<211> LENGTH: 299
<212> TYPE: PRT
<213> ORGANISM: Artificial
<220> FEATURE:
<223> OTHER INFORMATION: Amino acid sequence of cellulase HGD45
```

<400> SEQUENCE: 11

Met Arg Ser Thr Pro Val Leu Arg Thr Leu Ala Ala Ala Leu Pro
1               5                   10                  15

Leu Val Ala Ser Ala Ala Ser Gly Ser Gly Gln Ser Thr Arg Tyr Trp
            20                  25                  30

Asp Cys Cys Lys Pro Ser Cys Ala Trp Pro Gly Lys Ala Ala Val Ser
            35                  40                  45

Gln Pro Val Tyr Ala Cys Asp Ala Asn Phe Gln Arg Leu Ser Asp Phe
        50                  55                  60

Asn Val Gln Ser Gly Cys Asn Gly Gly Ser Ala Tyr Ser Cys Ala Asp
65                  70                  75                  80

Gln Thr Pro Trp Ala Val Asn Asp Asn Leu Ala Tyr Gly Phe Ala Ala
                85                  90                  95

Thr Ser Ile Ala Gly Gly Ser Glu Ser Ser Trp Cys Cys Ala Cys Tyr
            100                 105                 110

Ala Leu Thr Phe Thr Ser Gly Pro Val Ala Gly Lys Thr Met Val Val
        115                 120                 125

Gln Ser Thr Ser Thr Gly Gly Asp Leu Gly Ser Asn His Phe Asp Ile
130                 135                 140

Ala Met Pro Gly Gly Gly Val Gly Ile Phe Asn Gly Cys Ser Ser Gln
145                 150                 155                 160

Phe Gly Gly Leu Pro Gly Ala Gln Tyr Gly Gly Ile Ser Ser Arg Asp
                165                 170                 175

Gln Cys Asp Ser Phe Pro Ala Pro Leu Lys Pro Gly Cys Gln Trp Arg
            180                 185                 190

Phe Asp Trp Phe Gln Asn Ala Asp Asn Pro Thr Phe Thr Phe Gln Gln
        195                 200                 205

Val Gln Cys Pro Ala Glu Ile Val Ala Arg Ser Gly Cys Lys Arg Asn
            210                 215                 220

Asp Asp Ser Ser Phe Pro Val Phe Thr Pro Pro Ser Gly Gly Asn Gly
225                 230                 235                 240

Gly Thr Gly Thr Pro Thr Ser Thr Ala Pro Gly Ser Gly Gln Thr Ser
                245                 250                 255

Pro Gly Gly Gly Ser Gly Cys Thr Ser Gln Lys Trp Ala Gln Cys Gly
            260                 265                 270

Gly Ile Gly Phe Ser Gly Cys Thr Thr Cys Val Ser Gly Thr Thr Cys
        275                 280                 285

Gln Lys Leu Asn Asp Tyr Tyr Ser Gln Cys Leu
    290                 295

<210> SEQ ID NO 12
<211> LENGTH: 900
<212> TYPE: DNA
<213> ORGANISM: Artificial
<220> FEATURE:
<223> OTHER INFORMATION: Polynucleotide sequence of cellulase HGD45

<400> SEQUENCE: 12

```
atgcgatcta cccccggtcct ccgaaccacg ctcgccgccg ccctcccgct cgtggccagc     60
gccgcctctg gctctggcca gagcacgcga tactgggact gctgcaagcc ttcttgcgcc    120
tggcctggca aggccgccgt gtctcagcct gtgtacgcct gcgacgccaa cttccagcga    180
ctgtcggact tcaacgtcca gtcgggctgc aacggcggca gcgcctactc ttgcgccgac    240
cagacccctt gggccgtgaa cgacaacctc gcctacggct tcgccgccac gtctattgcc    300
```

```
ggcggcagcg agtcgtcttg gtgctgcgcc tgctacgccc tgacgttcac ctcgggcccg      360
gtcgccggca agacgatggt ggtgcagagc acctccacgg gcggcgacct gggctctaac      420
cacttcgaca ttgccatgcc gggcggcggc gtgggcattt caacggctg ctcgtctcag       480 ttcggcggcc ttccaggcgc ccagtacggc ggcattagct cgcgagacca gtgcgactct      540
ttccctgccc cgctgaagcc tggctgccag tggcgattcg actggttcca gaacgccgac      600
aaccctacct tcacgttcca gcaggtccag tgccctgccg agattgtggc ccgatcgggc      660
tgcaagcgaa acgacgacag ctcgttcccg gtgttcaccc ctccttctgg cggcaacggc      720
ggcacgggca cccctacgag caccgcgcca ggctctggcc agacgtctcc gggcggcggc      780
tctggctgca cgtctcagaa gtgggcccag tgcggcggca ttggcttctc tggctgcaca      840
acttgcgtgt cgggcacgac atgccagaag ctgaacgact actactctca gtgcctctga      900
```

<210> SEQ ID NO 13
<211> LENGTH: 86
<212> TYPE: PRT
<213> ORGANISM: Artificial
<220> FEATURE:
<223> OTHER INFORMATION: Amino acid sequence of barley-derived protease inhibitory peptide PCL

<400> SEQUENCE: 13

```
Ala Pro Gly Ser Ser Val Glu Lys Lys Pro Glu Gly Val Asn Thr Gly
1               5                   10                  15

Ala Gly Asp Arg His Asn Leu Lys Thr Glu Trp Pro Glu Leu Val Gly
                20                  25                  30

Lys Ser Val Glu Glu Ala Lys Lys Val Ile Leu Gln Asp Lys Pro Glu
            35                  40                  45

Ala Gln Ile Ile Val Leu Pro Val Gly Thr Ile Val Thr Met Glu Tyr
        50                  55                  60

Arg Ile Asp Arg Val Arg Leu Phe Val Asp Lys Leu Asp Asn Ile Ala
65                  70                  75                  80

Gln Val Pro Arg Val Gly
                85
```

<210> SEQ ID NO 14
<211> LENGTH: 261
<212> TYPE: DNA
<213> ORGANISM: Artificial
<220> FEATURE:
<223> OTHER INFORMATION: Polynucleotide sequence of barley-derived protease inhibitory peptide PCL

<400> SEQUENCE: 14

```
gcccccggct ccagcgtcga gaagaagccc gagggtgtca acaccggcgc cggtgatcgc       60
cacaacctca agaccgagtg gcccgaactc gtcggcaagt ccgtcgagga ggccaagaag      120
gtcatcctcc aagacaagcc cgaggcccag atcatcgtgc tccccgtcgg cacgatcgtc      180
accatggagt accgcatcga tcgcgtccgc ctcttcgtcg acaagctcga caacatcgcc      240
caagtccccc gagtcggcta g                                                261
```

<210> SEQ ID NO 15
<211> LENGTH: 364
<212> TYPE: PRT
<213> ORGANISM: Artificial
<220> FEATURE:
<223> OTHER INFORMATION: Amino acid sequence of fusion protein

<400> SEQUENCE: 15

```
Ala Ser Gly Ser Gly Gln Ser Thr Arg Tyr Trp Asp Cys Cys Lys Pro
 1               5                  10                  15

Ser Cys Ala Trp Pro Gly Lys Ala Ala Val Ser Gln Pro Val Tyr Ala
            20                  25                  30

Cys Asp Ala Asn Phe Gln Arg Leu Ser Asp Phe Asn Val Gln Ser Gly
            35                  40                  45

Cys Asn Gly Gly Ser Ala Tyr Ser Cys Ala Asp Gln Thr Pro Trp Ala
 50                  55                  60

Val Asn Asp Asn Leu Ala Tyr Gly Phe Ala Ala Thr Ser Ile Ala Gly
 65                  70                  75                  80

Gly Ser Glu Ser Ser Trp Cys Cys Ala Cys Tyr Ala Leu Thr Phe Thr
                85                  90                  95

Ser Gly Pro Val Ala Gly Lys Thr Met Val Val Gln Ser Thr Ser Thr
            100                 105                 110

Gly Gly Asp Leu Gly Ser Asn His Phe Asp Ile Ala Met Pro Gly Gly
            115                 120                 125

Gly Val Gly Ile Phe Asn Gly Cys Ser Ser Gln Phe Gly Gly Leu Pro
            130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
                165                 170                 175

Asn Ala Asp Asn Pro Thr Phe Thr Phe Gln Gln Val Gln Cys Pro Ala
            180                 185                 190

Glu Ile Val Ala Arg Ser Gly Cys Lys Arg Asn Asp Asp Ser Ser Phe
            195                 200                 205

Pro Val Phe Thr Pro Pro Ser Gly Gly Asn Gly Thr Gly Thr Pro
            210                 215                 220

Thr Ser Thr Ala Pro Gly Ser Gly Gln Thr Ser Pro Gly Gly Ser
225                 230                 235                 240

Gly Cys Thr Ser Gln Lys Trp Ala Gln Cys Gly Gly Ile Gly Phe Ser
                245                 250                 255

Gly Cys Thr Thr Cys Val Ser Gly Thr Thr Cys Gln Lys Leu Asn Asp
            260                 265                 270

Tyr Tyr Ser Gln Cys Leu Ala Pro Gly Ser Ser Val Glu Lys Lys Pro
            275                 280                 285

Glu Gly Val Asn Thr Gly Ala Gly Asp Arg His Asn Leu Lys Thr Glu
            290                 295                 300

Trp Pro Glu Leu Val Gly Lys Ser Val Glu Glu Ala Lys Lys Val Ile
305                 310                 315                 320

Leu Gln Asp Lys Pro Glu Ala Gln Ile Ile Val Leu Pro Val Gly Thr
            325                 330                 335

Ile Val Thr Met Glu Tyr Arg Ile Asp Arg Val Arg Leu Phe Val Asp
            340                 345                 350

Lys Leu Asp Asn Ile Ala Gln Val Pro Arg Val Gly
            355                 360
```

<210> SEQ ID NO 16
<211> LENGTH: 1095
<212> TYPE: DNA
<213> ORGANISM: Artificial
<220> FEATURE:
<223> OTHER INFORMATION: Polynucleotide sequence of fusion gene

<400> SEQUENCE: 16

```
gcctctggct ctggccagag cacgcgatac tgggactgct gcaagccttc ttgcgcctgg    60
cctggcaagg ccgccgtgtc tcagcctgtg tacgcctgcg acgccaactt ccagcgactg   120
tcggacttca acgtccagtc gggctgcaac ggcggcagcg cctactcttg cgccgaccag   180
accccttggg ccgtgaacga caacctcgcc tacggcttcg ccgccacgtc tattgccggc   240
ggcagcgagt cgtcttggtg ctgcgcctgc tacgccctga cgttcacctc gggcccggtc   300
gccggcaaga cgatggtggt gcagagcacc tccacgggcg cgacctggg ctctaaccac    360 ttcgacattg ccatgccggg cggcggcgtg gcattttca acggctgctc gtctcagttc    420
ggcggccttc caggcgccca gtacggcggc attagctcgc gagaccagtg cgactctttc   480
cctgccccgc tgaagcctgg ctgccagtgg cgattcgact ggttccagaa cgccgacaac   540
cctaccttca cgttccagca ggtccagtgc cctgccgaga ttgtggcccg atcgggctgc   600
aagcgaaacg acgacagctc gttcccggtg ttcaccccct cttctggcgg caacggcggc   660
acgggcaccc ctacgagcac cgcgccaggc tctggccaga cgtctccggg cggcggctct   720
ggctgcacgt ctcagaagtg ggcccagtgc ggcggcattg gcttctctgg ctgcacaact   780
tgcgtgtcgg gcacgacatg ccagaagctg aacgactact actctcagtg cctcgccccc   840
ggctccagcg tcgagaagaa gcccgagggt gtcaacaccg cgccggtga tcgccacaac   900 ctcaagaccg agtggcccga actcgtcggc aagtccgtcg aggaggccaa gaaggtcatc   960
ctccaagaca agcccgaggc ccagatcatc gtgctcccg tcggcacgat cgtcaccatg   1020
gagtaccgca tcgatcgcgt ccgcctcttc gtcgacaagc tcgacaacat cgcccaagtc   1080
ccccgagtcg gctag                                                    1095
```

<210> SEQ ID NO 17
<211> LENGTH: 41
<212> TYPE: DNA
<213> ORGANISM: Artificial
<220> FEATURE:
<223> OTHER INFORMATION: Primer

<400> SEQUENCE: 17

```
ctagtgtgcc tctagaggag cgggcctctg gctctggcca g                        41
```

<210> SEQ ID NO 18
<211> LENGTH: 39
<212> TYPE: DNA
<213> ORGANISM: Artificial
<220> FEATURE:
<223> OTHER INFORMATION: Primer

<400> SEQUENCE: 18

```
tcgacgctgg agccgggggc gaggcactga gagtagtag                           39
```

<210> SEQ ID NO 19
<211> LENGTH: 38
<212> TYPE: DNA
<213> ORGANISM: Artificial
<220> FEATURE:
<223> OTHER INFORMATION: Primer

<400> SEQUENCE: 19

```
ctactactct cagtgcctcg ccccggctc cagcgtcg                             38
```

<210> SEQ ID NO 20
<211> LENGTH: 37
<212> TYPE: DNA

<213> ORGANISM: Artificial
<220> FEATURE:
<223> OTHER INFORMATION: Primer

<400> SEQUENCE: 20
tcgccacgga gctttactag ccgactcggg ggacttg             37

<210> SEQ ID NO 21
<211> LENGTH: 293
<212> TYPE: PRT
<213> ORGANISM: Artificial
<220> FEATURE:
<223> OTHER INFORMATION: Amino acid sequence of cellulase NT45

<400> SEQUENCE: 21

Met Arg Ser Ser Thr Ile Leu Gln Thr Gly Leu Val Ala Ala Leu Pro
1               5                   10                  15

Phe Ala Val Gln Ala Ala Ser Gly Ser Gly Gln Ser Thr Arg Tyr Trp
            20                  25                  30

Asp Cys Cys Lys Pro Ser Cys Ser Trp Ser Gly Lys Ala Pro Val Asn
        35                  40                  45

Arg Pro Val Leu Ala Cys Asp Ala Asn Asn Asn Pro Leu Ser Asp Ala
    50                  55                  60

Ser Val Lys Ser Gly Cys Asp Gly Gly Ser Ala Tyr Thr Cys Ala Asn
65                  70                  75                  80

Asn Ser Pro Trp Ala Val Asn Asp Gln Leu Ala Tyr Gly Phe Ala Ala
                85                  90                  95

Thr Lys Leu Ser Gly Gly Thr Glu Ser Ser Trp Cys Cys Ala Cys Tyr
            100                 105                 110

Ala Leu Thr Phe Thr Ser Gly Pro Val Ala Gly Lys Thr Leu Val Val
        115                 120                 125

Gln Ser Thr Ser Thr Gly Gly Asp Leu Gly Ser Asn His Phe Asp Ile
    130                 135                 140

Asn Met Pro Gly Gly Gly Val Gly Leu Phe Asp Gly Cys Lys Arg Gln
145                 150                 155                 160

Phe Gly Gly Leu Pro Gly Ala Gln Tyr Gly Gly Ile Ser Ser Arg Ser
                165                 170                 175

Gln Cys Asp Ser Phe Pro Ala Ala Leu Lys Pro Gly Cys Gln Trp Arg
            180                 185                 190

Phe Asp Trp Phe Gln Asn Ala Asp Asn Pro Asn Phe Thr Phe Lys Gln
        195                 200                 205

Val Gln Cys Pro Ser Glu Leu Thr Ser Arg Thr Gly Cys Lys Arg Asn
    210                 215                 220

Asp Asp Ser Gln Phe Pro Val Phe Thr Pro Pro Ser Gly Gly Gly Ser
225                 230                 235                 240

Asn Pro Ser Thr Pro Thr Thr Pro Pro Ser Ser Gly Gly Ser Gly Ser
                245                 250                 255

Cys Thr Ala Asp Lys Tyr Ala Gln Cys Gly Gly Ser Gly Trp Ser Gly
            260                 265                 270

Cys Thr Asn Cys Pro Ser Gly Ser Thr Cys Lys Thr Ile Asn Asp Tyr
        275                 280                 285

Tyr His Gln Cys Ala
    290

<210> SEQ ID NO 22
<211> LENGTH: 882
<212> TYPE: DNA

<213> ORGANISM: Artificial
<220> FEATURE:
<223> OTHER INFORMATION: Polynucleotide sequence of cellulase NT45

<400> SEQUENCE: 22

```
atgcgctcct ccaccattct ccagaccggc ctcgtcgccg ccctcccctt cgccgtccag      60
gccgcctcgg gctcgggcca gtccaccgc tactgggact gctgcaagcc cagctgctcc     120
tggtcgggca aggcccccgt caaccgcccc gtcctcgcct cgacgccaa caacaacccc     180
ctgtcggacg ccagcgtcaa gtccggctgc gacgcggct ccgcctacac ctgcgccaac     240
aactcgccct gggccgtcaa cgaccagctc gcctacggct cgccgccac caagctgtcg     300
ggcggcacgg agagctcctg gtgctgcgcc tgctacgccc tcacctttac gtccggcccc     360
gtcgccggca agaccctcgt cgtccagagc acctccacgg cggcgacct gggcagcaac     420
cacttcgaca tcaacatgcc cggcggcggc gtcggcctct cgacggctg caagcgccag     480
tttggcggcc tgcccggcgc ccagtacggc ggcatttcga gccgcagcca gtgcgactcc     540
ttccccgccg ccctcaagcc cggctgccag tggcgcttcg actggtttca gaacgccgac     600
aaccccaact tcacctttaa gcaggtccag tgccctcgg agctgaccag ccgcacgggc     660
tgcaagcgca acgacgacag ccagttcccc gtctttaccc ccccctccgg cggcggctcg     720
aaccccagca cgcccaccac gccccctcc tcgggcggcg ctccggctg caccgccgac     780
aagtacgccc agtgcggcgg ctccggctgg tcgggctgca cgaactgccc cagcggctcc     840
acctgcaaga ccatcaacga ctactaccac cagtgcgcct aa                       882
```

<210> SEQ ID NO 23
<211> LENGTH: 64
<212> TYPE: PRT
<213> ORGANISM: Artificial
<220> FEATURE:
<223> OTHER INFORMATION: Amino acid sequence of marinostatin (MST)

<400> SEQUENCE: 23

```
Ala Pro Gly Thr Thr Pro Phe Phe Ala Asn Leu Leu Ala Ser Gln Thr
  1               5                  10                  15

Arg Glu Leu Thr Glu Asn Glu Leu Glu Met Thr Ala Gly Gly Thr Ala
             20                  25                  30

Ser Gln Gln Ser Pro Val Gln Glu Val Pro Glu Gln Pro Phe Ala Thr
         35                  40                  45

Met Arg Tyr Pro Ser Asp Ser Asp Glu Asp Gly Phe Asn Phe Pro Val
     50                  55                  60
```

<210> SEQ ID NO 24
<211> LENGTH: 192
<212> TYPE: DNA
<213> ORGANISM: Artificial
<220> FEATURE:
<223> OTHER INFORMATION: Polynucleotide sequence of marinostatin (MST)

<400> SEQUENCE: 24

```
gcccccggca ccaccccctt ctttgccaac ctcctcgcta gccagacccg cgagctcacc      60
gagaacgagc tcgagatgac cgctggcggt accgctagcc agcaaagccc cgtccaagag     120
gtccccgagc agcccttcgc caccatgcgc taccctagcg acagcgacga ggacggcttc     180
aacttccccg tc                                                         192
```

<210> SEQ ID NO 25
<211> LENGTH: 336

<212> TYPE: PRT
<213> ORGANISM: Artificial
<220> FEATURE:
<223> OTHER INFORMATION: Amino acid sequence of fusion protein

<400> SEQUENCE: 25

| Ala | Ser | Gly | Ser | Gly | Gln | Ser | Thr | Arg | Tyr | Trp | Asp | Cys | Cys | Lys | Pro |
|---|---|---|---|---|---|---|---|---|---|---|---|---|---|---|---|
| 1 | | | | 5 | | | | | 10 | | | | | 15 | |

Ser Cys Ser Trp Ser Gly Lys Ala Pro Val Asn Arg Pro Val Leu Ala
                20                  25                  30

Cys Asp Ala Asn Asn Pro Leu Ser Asp Ala Ser Val Lys Ser Gly
            35                  40                  45

Cys Asp Gly Gly Ser Ala Tyr Thr Cys Ala Asn Asn Ser Pro Trp Ala
50                  55                  60

Val Asn Asp Gln Leu Ala Tyr Gly Phe Ala Ala Thr Lys Leu Ser Gly
65                  70                  75                  80

Gly Thr Glu Ser Ser Trp Cys Cys Ala Cys Tyr Ala Leu Thr Phe Thr
                85                  90                  95

Ser Gly Pro Val Ala Gly Lys Thr Leu Val Val Gln Ser Thr Ser Thr
                100                 105                 110

Gly Gly Asp Leu Gly Ser Asn His Phe Asp Ile Asn Met Pro Gly Gly
            115                 120                 125

Gly Val Gly Leu Phe Asp Gly Cys Lys Arg Gln Phe Gly Gly Leu Pro
130                 135                 140

Gly Ala Gln Tyr Gly Gly Ile Ser Ser Arg Ser Gln Cys Asp Ser Phe
145                 150                 155                 160

Pro Ala Ala Leu Lys Pro Gly Cys Gln Trp Arg Phe Asp Trp Phe Gln
                165                 170                 175

Asn Ala Asp Asn Pro Asn Phe Thr Phe Lys Gln Val Gln Cys Pro Ser
                180                 185                 190

Glu Leu Thr Ser Arg Thr Gly Cys Lys Arg Asn Asp Asp Ser Gln Phe
            195                 200                 205

Pro Val Phe Thr Pro Pro Ser Gly Gly Ser Asn Pro Ser Thr Pro
210                 215                 220

Thr Thr Pro Pro Ser Ser Gly Gly Gly Ser Gly Cys Thr Ala Asp Lys
225                 230                 235                 240

Tyr Ala Gln Cys Gly Gly Ser Gly Trp Ser Gly Cys Thr Asn Cys Pro
                245                 250                 255

Ser Gly Ser Thr Cys Lys Thr Ile Asn Asp Tyr Tyr His Gln Cys Ala
                260                 265                 270

Ala Pro Gly Thr Thr Pro Phe Phe Ala Asn Leu Leu Ala Ser Gln Thr
            275                 280                 285

Arg Glu Leu Thr Glu Asn Glu Leu Glu Met Thr Ala Gly Gly Thr Ala
290                 295                 300

Ser Gln Gln Ser Pro Val Gln Glu Val Pro Glu Gln Pro Phe Ala Thr
305                 310                 315                 320

Met Arg Tyr Pro Ser Asp Ser Asp Glu Asp Gly Phe Asn Phe Pro Val
                325                 330                 335

<210> SEQ ID NO 26
<211> LENGTH: 1011
<212> TYPE: DNA
<213> ORGANISM: Artificial
<220> FEATURE:
<223> OTHER INFORMATION: Polynucleotide sequence of fusion gene

<400> SEQUENCE: 26

```
gcctcgggct cgggccagtc cacccgctac tgggactgct gcaagcccag ctgctcctgg    60
tcgggcaagg cccccgtcaa ccgcccgtc ctcgcctgcg acgccaacaa caaccccctg    120
tcggacgcca gcgtcaagtc cggctgcgac ggcggctccg cctacacctg cgccaacaac    180
tcgccctggg ccgtcaacga ccagctcgcc tacggcttcg ccgccaccaa gctgtcgggc    240
ggcacggaga gctcctggtg ctgcgcctgc tacgccctca cctttacgtc cggccccgtc    300
gccggcaaga ccctcgtcgt ccagagcacc tccacgggcg cgacctggg cagcaaccac    360 ttcgacatca acatgcccgg cggcggcgtc ggcctcttcg acggctgcaa gcgccagttt    420
ggcggcctgc ccgcgccca gtacggcggc atttcgagcc gcagccagtg cgactccttc    480
cccgccgccc tcaagcccgg ctgccagtgg cgcttcgact ggtttcagaa cgccgacaac    540
cccaacttca cctttaagca ggtccagtgc ccctcggagc tgaccagccg cacgggctgc    600
aagcgcaacg acgacagcca gttccccgtc tttaccccc cctccggcgg cggctcgaac    660
cccagcacgc ccaccacgcc ccctcctcg ggcggcggct ccggctgcac cgccgacaag    720
tacgcccagt gcggcggctc cggctggtcg ggctgcacga actgccccag cggctccacc    780
tgcaagacca tcaacgacta ctaccaccag tgcgccgccc ccggcaccac ccccttcttt    840
gccaacctcc tcgctagcca gacccgcgag ctcaccgaga acgagctcga gatgaccgct    900
ggcggtaccg ctagccagca aagcccgtc caagaggtcc ccgagcagcc cttcgccacc    960
atgcgctacc ctagcgacag cgacgaggac ggcttcaact tccccgtcta g          1011
```

<210> SEQ ID NO 27
<211> LENGTH: 41
<212> TYPE: DNA
<213> ORGANISM: Artificial
<220> FEATURE:
<223> OTHER INFORMATION: Primer

<400> SEQUENCE: 27
ctagtgtgcc tctagaggag cgggcctcgg gctcgggcca g                         41

<210> SEQ ID NO 28
<211> LENGTH: 39
<212> TYPE: DNA
<213> ORGANISM: Artificial
<220> FEATURE:
<223> OTHER INFORMATION: Primer

<400> SEQUENCE: 28 aaggggggtgg tgccgggggc ggcgcactgg tggtagtag                           39

<210> SEQ ID NO 29
<211> LENGTH: 39
<212> TYPE: DNA
<213> ORGANISM: Artificial
<220> FEATURE:
<223> OTHER INFORMATION: Primer

<400> SEQUENCE: 29
ctactaccac cagtgcgccg ccccggcac cacccccctt                            39

<210> SEQ ID NO 30
<211> LENGTH: 40
<212> TYPE: DNA
<213> ORGANISM: Artificial
<220> FEATURE:
<223> OTHER INFORMATION: Primer

<400> SEQUENCE: 30
tcgccacgga gctttactag acggggaagt tgaagccgtc          40

<210> SEQ ID NO 31
<211> LENGTH: 84
<212> TYPE: PRT
<213> ORGANISM: Artificial
<220> FEATURE:
<223> OTHER INFORMATION: Amino acid sequence of propeptide PPS

<400> SEQUENCE: 31

Ala Glu Glu Ala Lys Glu Lys Tyr Leu Ile Gly Phe Asn Glu Gln Glu
1               5                   10                  15

Ala Val Ser Glu Phe Val Glu Gln Ile Glu Ala Asn Asp Glu Val Ala
            20                  25                  30

Ile Leu Ser Glu Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met

<210> SEQ ID NO 32
<211> LENGTH: 252
<212> TYPE: DNA
<213> ORGANISM: Artificial
<220> FEATURE:
<223> OTHER INFORMATION: Polynucleotide sequence of propeptide PPS

<400> SEQUENCE: 32
gccgaggagg ccaaggagaa gtacctcatc ggcttcaacg agcaagaggc cgtcagcgag          60
ttcgtcgagc agatcgaggc caacgacgag gtcgccattc tcagcgagga ggaggaggtc         120
gagatcgagc tcctccacga gttcgagacc atccccgtcc tcagcgtcga gctcagcccc         180
gaggacgtcg acgctctcga gctcgacccc gccatcagct acatcgagga ggacgccgag         240
gtcaccacca tg                                                              252

<210> SEQ ID NO 33
<211> LENGTH: 351
<212> TYPE: PRT
<213> ORGANISM: Artificial
<220> FEATURE:
<223> OTHER INFORMATION: Amino acid sequence of fusion protein

<400> SEQUENCE: 33

Ala Glu Glu Ala Lys Glu Lys Tyr Leu Ile Gly Phe Asn Glu Gln Glu
1               5                   10                  15

Ala Val Ser Glu Phe Val Glu Gln Ile Glu Ala Asn Asp Glu Val Ala
            20                  25                  30

Ile Leu Ser Glu Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met Ala Asp Gly Arg Ser Thr Arg Tyr Trp Asp Cys Cys
                85                  90                  95

```
Lys Pro Ser Cys Gly Trp Ala Lys Lys Ala Ser Val Asn Gln Pro Val
            100                 105                 110

Phe Ser Cys Asn Ala Asn Phe Gln Arg Ile Thr Asp Phe Asp Ala Lys
        115                 120                 125

Ser Gly Cys Glu Pro Gly Val Ala Tyr Ser Cys Ala Asp Gln Thr
    130                 135                 140

Pro Trp Ala Val Asn Asp Asn Phe Ser Leu Gly Phe Ala Ala Thr Ser
145                 150                 155                 160

Ile Ala Gly Ser Asn Glu Ala Gly Trp Cys Cys Ala Cys Tyr Glu Leu
                165                 170                 175

Thr Phe Thr Ser Gly Pro Val Ala Gly Lys Lys Met Val Val Gln Ser
            180                 185                 190

Thr Ser Thr Gly Gly Asp Leu Gly Ser Asn His Phe Asp Leu Asn Ile
            195                 200                 205

Pro Gly Gly Gly Val Gly Ile Phe Asp Gly Cys Thr Pro Gln Phe Gly
        210                 215                 220

Gly Leu Pro Gly Gln Arg Tyr Gly Gly Ile Ser Ser Arg Asn Glu Cys
225                 230                 235                 240

Asp Ser Phe Pro Asp Ala Leu Lys Pro Gly Cys Tyr Trp Arg Phe Asp
                245                 250                 255

Trp Phe Lys Asn Ala Asp Asn Pro Ser Phe Ser Phe Arg Gln Val Gln
            260                 265                 270

Cys Pro Ala Glu Leu Val Ala Arg Thr Gly Cys Arg Arg Asn Asp Asp
            275                 280                 285

Gly Asn Phe Pro Ala Val Gln Ile Pro Ser Ser Thr Ser Ser Ser
    290                 295                 300

Pro Pro Val Gln Pro Thr Thr Pro Ser Gly Cys Thr Ala Glu Arg Trp
305                 310                 315                 320

Ala Gln Cys Gly Gly Asn Gly Trp Ser Gly Cys Thr Cys Val Ala
                325                 330                 335

Gly Ser Thr Cys Thr Lys Ile Asn Asp Trp Tyr His Gln Cys Leu
            340                 345                 350

<210> SEQ ID NO 34
<211> LENGTH: 1056
<212> TYPE: DNA
<213> ORGANISM: Artificial
<220> FEATURE:
<223> OTHER INFORMATION: Polynucleotide sequence of fusion gene

<400> SEQUENCE: 34
gccgaggagg ccaaggagaa gtacctcatc ggcttcaacg agcaagaggc cgtcagcgag      60
ttcgtcgagc agatcgaggc caacgacgag gtcgccattc tcagcgagga ggaggaggtc     120
gagatcgagc tcctccacga gttcgagacc atccccgtcc tcagcgtcga gctcagcccc     180
gaggacgtcg acgctctcga gctcgacccc gccatcagct acatcgagga ggacgccgag     240
gtcaccacca tggctgatgg caggtccacc cgctactggg actgctgcaa gccttcgtgc     300
ggctgggcca agaaggctgg cgtgaaccag cctgtctttt cctgcaacgc caacttccag     360
cgtatcacgg acttcgacgc caagtccggc tgcgagccgg cggtgtcgc ctactcgtgc     420 gccgaccaga ccccatgggc tgtgaacgac aacttcagcc tcggttttgc tgccacctct     480
attgccggca gcaatgaggc gggctggtgc tgcgcctgct acgagctcac cttcacatcc     540
ggtcctgttg ctggcaagaa gatggtcgtc cagtccacca gcactggcgg tgatcttggc     600
agcaaccact cgatctcaa catccccggc ggcggcgtcg gcatcttcga cggatgcact     660
```

-continued

```
cccccagttcg gcggtctgcc cggccagcgc tacggcggca tctcgtcccg caacgagtgc      720
gatagcttcc ccgacgccct caagcccggc tgctactggc gcttcgactg gttcaagaac      780
gccgacaatc cgagcttcag cttccgtcag gtccagtgcc cagccgagct cgtcgctcgc      840
accggatgcc gccgcaacga cgacggcaac ttccctgccg tccagatccc ctccagcagc      900
accagctcta gcccgccagt ccagcctacg actcccagcg gctgcactgc tgagaggtgg      960
gctcagtgcg gcggcaatgg ctggagcggc tgcaccacct gcgtcgctgg cagcacttgc     1020
acgaagatta atgactggta tcatcagtgc ctgtag                                1056
```

<210> SEQ ID NO 35
<211> LENGTH: 44
<212> TYPE: DNA
<213> ORGANISM: Artificial
<220> FEATURE:
<223> OTHER INFORMATION: Primer

<400> SEQUENCE: 35

```
ctagtgtgcc tctagaggag cgggccgagg aggccaagga gaag                         44
```

<210> SEQ ID NO 36
<211> LENGTH: 43
<212> TYPE: DNA
<213> ORGANISM: Artificial
<220> FEATURE:
<223> OTHER INFORMATION: Primer

<400> SEQUENCE: 36

```
agcgggtgga cctgccatca gccatggtgg tgacctcggc gtc                          43
```

<210> SEQ ID NO 37
<211> LENGTH: 43
<212> TYPE: DNA
<213> ORGANISM: Artificial
<220> FEATURE:
<223> OTHER INFORMATION: Primer

<400> SEQUENCE: 37

```
gacgccgagg tcaccaccat ggctgatggc aggtccaccc gct                          43
```

<210> SEQ ID NO 38
<211> LENGTH: 40
<212> TYPE: DNA
<213> ORGANISM: Artificial
<220> FEATURE:
<223> OTHER INFORMATION: Primer

<400> SEQUENCE: 38

```
tcgccacgga gctttactac aggcactgat gataccagtc                              40
```

<210> SEQ ID NO 39
<211> LENGTH: 291
<212> TYPE: PRT
<213> ORGANISM: Artificial
<220> FEATURE:
<223> OTHER INFORMATION: Amino acid sequence of lipase TG

<400> SEQUENCE: 39

Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
                20                  25                  30

```
Asn Leu Phe Ala Gln Tyr Ser Ala Ala Tyr Cys Gly Lys Asn Asn
         35                  40                  45

Asp Ala Pro Ala Gly Thr Asn Ile Thr Cys Thr Gly Asn Ala Cys Pro
 50                  55                  60

Glu Val Glu Lys Ala Asp Ala Thr Phe Leu Tyr Ser Phe Glu Gly Ser
65                  70                  75                  80

Gly Val Gly Asp Val Thr Gly Phe Leu Ala Leu Asp Asn Thr Asn Lys
                 85                  90                  95

Leu Ile Val Leu Ser Phe Arg Gly Ser Arg Ser Ile Glu Asn Trp Ile
                100                 105                 110

Gly Asn Leu Lys Phe Leu Met Lys Glu Ile Asn Asp Ile Cys Ser Gly
                115                 120                 125

Cys Arg Gly His Asp Gly Phe Thr Ser Ser Trp Arg Ser Val Ala Asp
130                 135                 140

Thr Leu Arg Gln Lys Val Glu Asp Ala Val Arg Glu His Pro Asp Tyr
145                 150                 155                 160

Arg Val Val Phe Thr Gly His Ser Leu Gly Gly Ala Leu Ala Thr Val
                165                 170                 175

Ala Gly Ala Asp Leu Arg Gly Asn Gly Tyr Asp Ile Asp Val Phe Ser
                180                 185                 190

Tyr Gly Ala Pro Arg Val Gly Asn Arg Ala Phe Ala Glu Phe Leu Thr
                195                 200                 205

Val Gln Thr Gly Gly Thr Leu Tyr Arg Ile Thr His Thr Asn Asp Ile
                210                 215                 220

Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Thr Arg Asn Asp
                245                 250                 255

Ile Val Lys Ile Glu Gly Ile Asp Ala Thr Gly Gly Asn Asn Arg Pro
                260                 265                 270

Asn Ile Pro Asp Ile Pro Ala His Leu Trp Tyr Phe Gly Leu Ile Gly
                275                 280                 285

Thr Cys Leu
    290

<210> SEQ ID NO 40
<211> LENGTH: 873
<212> TYPE: DNA
<213> ORGANISM: Artificial
<220> FEATURE:
<223> OTHER INFORMATION: Polynucleotide sequence of lipase TG

<400> SEQUENCE: 40
atgcgcagca gcctcgtgct gttctttgtc tccgcttgga ccgctctcgc cagccctatt      60
cgccgcgagg tctcccaaga tctcttcaac cagttcaacc tcttcgccca atactccgct     120
gccgcctact gcggtaagaa caacgacgcc cccgccggta cgaacattac ttgtaccggc     180
aacgcttgtc ccgaggtcga gaaggccgac gccaccttcc tctacagctt tgagggcagc     240
ggcgtcggtg atgtcacggg cttttttagcc ctcgacaaca ccaacaagct catcgtcctc     300
agcttccgcg gtagccgcag catcgaaaac tggatcggca acctcaagtt tttaatgaag     360
gagatcaacg acatctgctc cggctgccgc ggtcacgacg gtttcacctc cagctggcgc     420
tccgtcgccg acacgctgcg ccaaaaggtc gaggacgccg tgcgcgagca ccccgactac     480
cgcgtcgtct tcaccggcca ctcttttaggt ggtgccctcg ccaccgtcgc tggcgccgat     540
```

```
ctccgcggca acggctacga cattgacgtc ttcagctatg cgctcctcg cgtcggcaat      600 cgcgcctttg ccgagttcct caccgtccag accggcggca ctttataccg catcacccac      660
accaacgata ttgtccccg tttaccccct cgcgagttcg gctattccca cagctccccc      720
gagtactgga tcaagagcgg cacgctggtc cccgtcaccc gcaacgatat cgtcaagatc      780
gagggcattg acgccacggg tggcaacaac cgccccaaca tccccgacat ccccgcccac      840
ctctggtact cggtttaat cggcacttgt ctc                                   873
```

<210> SEQ ID NO 41
<211> LENGTH: 385
<212> TYPE: PRT
<213> ORGANISM: Artificial
<220> FEATURE:
<223> OTHER INFORMATION: Amino acid sequence of fusion protein

<400> SEQUENCE: 41

```
Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Gly Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Lys Phe Leu
                85                  90                  95

Met Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Arg Pro Asn Ile Pro Asp Ile Pro
                245                 250                 255

Ala His Leu Trp Tyr Phe Gly Leu Ile Gly Thr Cys Leu Ala Pro Gly
            260                 265                 270

Asp Ala Pro Ser Ala Leu Tyr Ala Pro Ser Ala Leu Val Leu Thr Val
        275                 280                 285

Gly Lys Gly Val Ser Ala Thr Thr Ala Ala Pro Glu Arg Ala Val Thr
    290                 295                 300
```

```
Leu Thr Cys Ala Pro Gly Pro Ser Gly Thr His Pro Ala Ala Gly Ser
305                 310                 315                 320

Ala Cys Ala Asp Leu Ala Ala Val Gly Gly Asp Leu Asn Lys Ile Thr
                325                 330                 335

Arg Gly Glu Asp Val Met Cys Pro Pro Val Tyr Asp Pro Val Leu Leu
            340                 345                 350

Thr Val Cys Gly Val Trp Gln Gly Lys Arg Val Ser Tyr Glu Arg Val
        355                 360                 365

Phe Glu Asn Glu Cys Glu Met Asn Ala His Gly Ser Ser Val Phe Ala
    370                 375                 380

Phe
385

<210> SEQ ID NO 42
<211> LENGTH: 1158
<212> TYPE: DNA
<213> ORGANISM: Artificial
<220> FEATURE:
<223> OTHER INFORMATION: Polynucleotide sequence of fusion gene

<400> SEQUENCE: 42
gaggtctccc aagatctctt caaccagttc aacctcttcg cccaatactc cgctgccgcc      60
tactgcggta agaacaacga cgcccccgcc ggtacgaaca ttacttgtac cggcaacgct     120
tgtcccgagg tcgagaaggc cgacgccacc ttcctctaca gctttgaggg cagcggcgtc     180
ggtgatgtca cgggcttttt agccctcgac aacaccaaca agctcatcgt cctcagcttc     240
cgcggtagcc gcagcatcga aaactggatc ggcaacctca gttttttaat gaaggagatc     300
aacgacatct gctccggctg ccgcggtcac gacggtttca cctccagctg gcgctccgtc     360
gccgacacgc tgcgccaaaa ggtcgaggac gccgtgcgcg agcaccccga ctaccgcgtc     420
gtcttcaccg gccactcttt aggtggtgcc ctcgccaccg tcgctggcgc cgatctccgc     480
ggcaacggct acgacattga cgtcttcagc tatggcgctc ctcgcgtcgg caatcgcgcc     540
tttgccgagt tcctcaccgt ccagaccggc ggcactttat accgcatcac ccacaccaac     600
gatattgtcc ccgtttacc ccctcgcgag ttcggctatt cccacagctc ccccgagtac     660
tggatcaaga gcggcacgct ggtccccgtc acccgcaacg atatcgtcaa gatcgagggc     720
attgacgcca cgggtggcaa caaccgcccc aacatccccg acatccccgc ccacctctgg     780
tacttcggtt taatcggcac ttgtctcgcc ccgggcgatg ccccgagcgc cctctacgcc     840
cctagcgccc tcgtcctcac cgtcggaaag ggcgtcagcg ccacgaccgc cgccccggag     900
cgcgccgtca ccctcacttg tgccccgggc ccgagcggca cccaccggc cgccggcagc     960 gcttgtgccg acctcgccgc cgtcggcggc gacctcaaca agattacccg cggcgaggac    1020
gtcatgtgtc cgccggtcta cgacccggtc ctcctcaccg tctgtggcgt ctggcaaggt    1080
aagcgcgtca gctacgagcg cgtgttcgag aacgagtgcg agatgaacgc ccacggcagc    1140
agcgtcttcg ctttctag                                                 1158

<210> SEQ ID NO 43
<211> LENGTH: 44
<212> TYPE: DNA
<213> ORGANISM: Artificial
<220> FEATURE:
<223> OTHER INFORMATION: Primer

<400> SEQUENCE: 43
ctagtgtgcc tctagaggag cgggaggtct cccaagatct cttc                      44
```

```
<210> SEQ ID NO 44
<211> LENGTH: 40
<212> TYPE: DNA
<213> ORGANISM: Artificial
<220> FEATURE:
<223> OTHER INFORMATION: Primer

<400> SEQUENCE: 44
ctcggggcat cgcccggggc gagacaagtg ccgattaaac           40

<210> SEQ ID NO 45
<211> LENGTH: 40
<212> TYPE: DNA
<213> ORGANISM: Artificial
<220> FEATURE:
<223> OTHER INFORMATION: Primer

<400> SEQUENCE: 45
gtttaatcgg cacttgtctc gccccgggcg atgccccgag           40
```